US009839684B2

(12) United States Patent
Andrieu et al.

(10) Patent No.: US 9,839,684 B2
(45) Date of Patent: Dec. 12, 2017

(54) PHARMACEUTICAL COMPOSITIONS COMPRISING INACTIVATED HIV VIRAL PARTICLES AND NON-PATHOGENIC LACTOBACILLI FOR THE INDUCTION OF ANTIGEN-SPECIFIC IMMUNOTOLERANCE

(75) Inventors: Jean-Marie Andrieu, Paris (FR); Louis Lu, Bejing (CN)

(73) Assignees: BIOVAXIM LIMITED, London (GB); UNIVERSITE PARIS DESCARTES, Paris (FR); INSTITUT DE RECHERSCHE POUR LE DEVELOPPEMENT (IRD), Marseilles (FR)

( * ) Notice: Subject to any disclaimer, the term of this patent is extended or adjusted under 35 U.S.C. 154(b) by 586 days.

(21) Appl. No.: 14/009,250

(22) PCT Filed: Apr. 6, 2012

(86) PCT No.: PCT/IB2012/000857
§ 371 (c)(1),
(2), (4) Date: Jun. 10, 2014

(87) PCT Pub. No.: WO2012/137071
PCT Pub. Date: Oct. 11, 2012

(65) Prior Publication Data
US 2014/0302089 A1   Oct. 9, 2014

Related U.S. Application Data

(63) Continuation of application No. PCT/CN2011/072481, filed on Apr. 6, 2011, and a continuation of application No. PCT/CN2012/070761, filed on Jan. 30, 2012.

(60) Provisional application No. 61/534,088, filed on Sep. 13, 2011, provisional application No. 61/609,051, filed on Mar. 9, 2012.

(51) Int. Cl.
| A61K 39/21 | (2006.01) |
| A61K 39/15 | (2006.01) |
| A61K 39/39 | (2006.01) |
| A61K 39/12 | (2006.01) |
| A61K 39/09 | (2006.01) |
| A61K 39/00 | (2006.01) |

(52) U.S. Cl.
CPC .............. *A61K 39/15* (2013.01); *A61K 39/12* (2013.01); *A61K 39/21* (2013.01); *A61K 39/39* (2013.01); *A61K 39/09* (2013.01); *A61K 2039/523* (2013.01); *A61K 2039/5252* (2013.01); *A61K 2039/54* (2013.01); *A61K 2039/541* (2013.01); *A61K 2039/542* (2013.01); *A61K 2039/545* (2013.01); *A61K 2039/55594* (2013.01); *C12N 2740/16034* (2013.01); *C12N 2740/16234* (2013.01)

(58) Field of Classification Search
CPC .................. A61K 39/21; A61K 39/09; A61K 2039/55594; C12N 2740/16034
See application file for complete search history.

(56) References Cited

U.S. PATENT DOCUMENTS

| 5,895,758 A * | 4/1999 | Majnarich ................. C12R 1/25 424/93.45 |
| 2004/0009937 A1 | 1/2004 | Chen et al. |
| 2006/0093623 A1* | 5/2006 | Andrieu .................... C12N 7/00 424/208.1 |
| 2009/0087451 A1* | 4/2009 | Buller .................. A61K 39/275 424/201.1 |

FOREIGN PATENT DOCUMENTS

| CN | 1387442 A | 12/2002 |
| CN | 1646020 A | 7/2005 |
| JP | 2008-532498 A | 8/2008 |
| WO | WO-01/21200 A1 | 3/2001 |
| WO | WO-01/31046 A1 | 5/2001 |
| WO | WO-03/063786 A2 | 8/2003 |
| WO | WO-2006/012320 A2 | 2/2006 |
| WO | WO-2006/123256 A2 | 11/2006 |
| WO | WO-2009/093900 A1 | 7/2009 |

OTHER PUBLICATIONS

Davidson, L, et al., 2011, Lactobacillus GG as an immune adjuvant for live-attenuated influenza vaccine in healthy adults: a randomized double-blind placebo-controlled trial, Eur. J. Clin. Nutrition 65:501-507 (published online Feb. 2, 2011).*
Reynolds et al., "Macaques vaccinated with live-attenuated SIV control replication of heterologous virus," Journal of Experimental Medicine, vol. 205, No. 11, Oct. 6, 2008, pp. 2537-2550.
Aires et al., "Production of Human Papillomavirus Type 16 L1 Virus-Like Particles by Recombinant *Lactobacillus casei* Cells," Applied and Environmental Microbiology, 2006, vol. 72, No. 1, pp. 745-752.
Beignon et al., "Lentiviral Vector-Based Prime/Boost Vaccination Against AIDS: Pilot Study Shows Protection Against Simian Immunodeficiency Virus SIVmac251 Challenge in Macaques," Journal of Virology, 2009, vol. 83, No. 21, pp. 10963-10974.
Chapman et al., "Recombinant *Mycobacterium bovis* BCG as an HIV Vaccine Vector," Current HIV Research, 2010, vol. 8, pp. 282-298.
Chege et al., "A prime-boost immunisation regimen using recombinant BCG and Pr55$^{gag}$ virus-like particle vaccines based on HIV type 1 subtype C successfully elicits Gag-specific responses in baboons," Vaccine, 2009, vol. 27, pp. 4857-4866.

(Continued)

*Primary Examiner* — Jeffrey Parkin
(74) *Attorney, Agent, or Firm* — Potomac Law Group, PLLC

(57) ABSTRACT

The present invention relates to pharmaceutical compositions comprising a mixture of a specific HIV antigen and a non-pathogenic living bacterium. Said specific HIV antigen comprises one or more epitopes from Gag and/or Pol proteins and is preferably under a particulate form. Said bacterium is preferably *Lactobacillus plantarum*. These compositions are useful for preventing and/or treating an HIV disease in humans.

11 Claims, 19 Drawing Sheets

(56) References Cited

OTHER PUBLICATIONS

Fang et al., "Modulation of humoral immune response through probiotic intake," FEMS Immunology and Medical Microbiology, 2000, vol. 29, pp. 47-52.

Faria et al., "Oral Tolerance: Therapeutic implications for autoimmune diseases," Clinical & Developmental Immunology, 2006, vol. 13, No. 2-4, pp. 143-157.

Grangette et al., "Mucosal Immune Responses and Protection Against Tetanus Toxin After Intranasal Immunization with Recombinant *Lactobacillus plantarum*," Infection and Immunity, 2001, vol. 69, No. 3, pp. 1547-1553.

Greene et al., "Extralymphoid CD8+ T Cells Resident in Tissue from Simian Immunodeficiency Virus SIVmac239Δnef-Vaccinated Macaques Suppress SIVmac239 Replication Ex Vivo," Journal of Virology, 2010, vol. 84, No. 7, pp. 3362-3372.

International Search Report and Written Opinion for Application No. PCT/EP2010/066977 dated Feb. 14, 2011.

International Search Report and Written Opinion for Application No. PCT/IB2012/000857 dated Oct. 18, 2012.

International Search Report for Application No. PCT/CN2011/072479 dated Jan. 19, 2012.

Kakarla, "Recombinant Lactobacillus as a Vaccine Vector for HIV," A thesis submitted to the Graduate Faculty of North Carolina State University in partial fulfillment of the requirements for the Degree of Master of Science, Immunology, Raleigh 2006, URL:http://repository.lib.ncsu.edu/ir/bits/tream/1840.16/2949/1/etd.pdf, 100 pages.

Karpenko et al., "Comparative analysis using a mouse model of the immunogenicity of artificial VLP and attenuated *Salmonella* strain carrying a DNA-vaccine encoding HIV-1 polyepitope CTL-immunogen," Vaccine, 2004, vol. 22, pp. 1692-1699.

Kinter et al., "CD25+ CD4+ Regulatory T Cells from the Peripheral Blood of Asymptomatic HIV-infected Individuals Regulate CD4+ and CD8+ HIV-specific T Cell Immune Responses In Vitro and Are Associated with Favorable Clinical Markers of Disease Status," The Journal of Experimental Medicine, 2004, vol. 200, No. 3, pp. 331-343.

Leenaars et al., "Comparison of adjuvants for immune potentiating properties and side effects in mice," Veterinary Immunology and Immunopathology, 1995, vol. 48, pp. 123-138.

Mestecky et al, "Perspectives on Mucosal Vaccines: Is Mucosal Tolerance a Barrier?," Journal of Immunology, 2007, vol. 179, No. 9, pp. 5633-5638.

Mohamadzadeh et al., "Lactobacilli activate human dendritic cells that skew T cells toward T helper 1 polarization," PNAS, 2005, vol. 102, No. 8, pp. 2880-2885.

Nardelli-Haefliger et al., "Human Papillomavirus Type 16 Virus-Like Particles Expressed in Attenuated *Salmonella typhimurium* Elicit Mucosal and Systemic Neutralizing Antibodies in Mice," Infection and Immunity, 1997, vol. 65, No. 8, pp. 3328-3336.

Spentzou et al., "Viral Inhibition Assay: A CD8 T Cell Neutralization Assay for Use in Clinical Trials of HIV-1 Vaccine Candidates," The Journal of Infectious Diseases, 2010, vol. 201, No. 5, pp. 720-729.

Speth et al., "Human immunodeficiency virus type-1 (HIV-1) Pr55$^{gag}$ virus-like particles are potent activators of human monocytes," Virology, 2008, vol. 382, pp. 46-58.

Weiner et al., "Oral Tolerance," Immunol Rev., 2005, vol. 206, pp. 232-259.

Xin et al., "Immunogenicity and protective efficacy of orally administered recombinant *Lactococcus lactis* expressing surface-bound HIV Env," Blood, 2003, vol. 102, No. 1, pp. 223-228.

Yu et al., "Generation of Mucosal Anti-Human Immunodeficiency Virus Type 1 T-Cell Responses by Recombinant *Mycobacterium smegmatis*," Clinical and Vaccine Immunology, 2006, vol. 13, No. 11, pp. 1204-1211.

Communication under Rule 71 (3) EPC—Intention to Grant issued in application No. 12 721 921.0 dated Dec. 22, 2015.

Intention to Grant issued in corresponding European application No. 12 721 921 dated Dec. 22, 2015.

Lu et al., "Therapeutic dendritic-cell vaccine for simian AIDS," Nature Medicine, vol. 9, No. 1, pp. 27-32, Jan. 2003.

Lu et al., "Therapeutic dendritic-cell vaccine for chronic HIV-1 infection," Nature Medicine, pp. 1-7, advanced online publication, Nov. 28, 2004.

Lu et al., "Induction of CD8+ Regulatory T Cells Protects Macaques against SIV Challenge," Cell Reports, vol. 2, pp. 1736-1746, Dec. 2012.

Andrieu et al., "Mucosal SIV vaccine comprising inactivated virus particles and bacterial adjuvants induce CD8+ T-regulatory cells that suppress SIV-positive CD4+ T-cell activation and prevent SIV infection in the macaque model," Frontiers in Immunology, vol. 5, Article 297, pp. 1-11, Jun. 2014.

Lu et al., "Suppression of HIV Replication by CD8+ Regulatory T-Cells in Elite Controllers," Frontiers in Immunology, vol. 7, Article 134, pp. 1-10, Apr. 2016.

Rein, Advances in Virology, vol. 2011, Article ID 403419, pp. 1-14, 2011.

Britton, HIV & Virology News 3, pp. 3-5, 2016.

Brennan, John, "Types of Non-Pathogenic Bacteria," eHow, accessed at http://www.ehow.com/list_6535062_types-non_pathogenic-bacteria.htm on Jan. 9, 2015.

* cited by examiner

SEQUENCE LISTING

```
<160> NUMBER OF SEQ ID NOS: 3

<210> SEQ ID NO 1
<211> LENGTH: 24
<212> TYPE: DNA
<213> ORGANISM: Artificial
<220> FEATURE:
<223> OTHER INFORMATION: sense PCR primer

<400> SEQUENCE: 1
gaggaaaaga aatttggagc agaa                                          24

<210> SEQ ID NO 2
<211> LENGTH: 21
<212> TYPE: DNA
<213> ORGANISM: Artificial
<220> FEATURE:
<223> OTHER INFORMATION: antisense PCR primer

<400> SEQUENCE: 2
gcttgatggt ctcccacaca a                                             21

<210> SEQ ID NO 3
<211> LENGTH: 35
<212> TYPE: DNA
<213> ORGANISM: Artificial
<220> FEATURE:
<223> OTHER INFORMATION: probe
<220> FEATURE:
<221> NAME/KEY: misc_binding
<222> LOCATION: (1)..(1)
<223> OTHER INFORMATION: The probe can be 5'-labeled with FAM
<220> FEATURE:
<221> NAME/KEY: misc_binding
<222> LOCATION: (35)..(35)
<223> OTHER INFORMATION: The probe can be 3'-labeled with TAMRA

<400> SEQUENCE: 3
aaagttgcac cccctatgac attaatcaga tgtta                              35
```

PHARMACEUTICAL COMPOSITIONS COMPRISING INACTIVATED HIV VIRAL PARTICLES AND NON-PATHOGENIC LACTOBACILLI FOR THE INDUCTION OF ANTIGEN-SPECIFIC IMMUNOTOLERANCE

The present invention relates to pharmaceutical compositions comprising a mixture of a specific HIV antigen and a non-pathogenic bacterium. Said specific HIV antigen comprises one or more epitopes from Gag and/or Pol proteins and is preferably under a particulate form. Said bacterium is preferably *Lactobacillus plantarum*. These compositions are useful for preventing and/or treating an HIV disease in humans.

BACKGROUND TO THE INVENTION

More than twenty five years after the discovery of human immunodeficiency virus (HIV), recent projections from the World Health Organization and the Joint United Nations Program on HIV/AIDS indicate that if the pandemic progresses at its current rate, there will be more than 30 million infections by 2011.

However, despite considerable research efforts for finding effective treatments for preventing HIV infections, the two recently tested preventive vaccines either have failed (Mc Elrath et al., 2008) or produced modest results (Rerks-Ngarm et al., 2009).

Jae-Sung Yu et al. (Clinical and Vaccine Immunology, November 2006, vol 13, No. 11, 1204-1211) described recombinant *Mycobacterium smegmatis* vectors constructed to express the HIV-1 group M consensus env gene CON6 either as a surface, intracellular, or secreted protein. The authors could demonstrate that, in mice, recombinant *M. smegmatis* was immunogenic for the induction of HIV-1 T-cell responses at mucosal surfaces.

Ke-Qin Xin et al. (Blood, 1 Jul. 2003, vol 102, No. 1, 223-228) described a recombinant *Lactococcus lactis* vector expressing the V2-V4 loop of HIV-1 Env on its cell surface. Oral immunization of mice with this vector induced:
  both mucosal and humoral immune responses as shown by detecting high levels of HIV-specific serum IgG and fecal IgA antibodies; and
  a cellular immune response as shown by an increased number of HIV-specific IFN-gamma-secreting cells.

To be properly expressed on the *L. lactis* cell surface, gene segments of 1 kb or less could be used.

Most scientists involved in HIV pathogenesis and prevention feel that before testing HIV preventive vaccines or other biological compositions for preventing or treating HIV infection in human beings, it would be more constructive to test their counterparts in non human primates (Morgan C, et al., 2008). The non human primate of choice is the macaque rhesus and among macaques, it has now been conclusively shown that macaques of Chinese origin infected by the Simian Immunodeficiency Virus (SIV) 239 are the best model mimicking most of the clinical, virologic and immunologic aspects of the evolution of HIV infection in humans (Marcondes M C, et al. 2006; Stahl-Hennig C, et al. 2007; Chen S, et al. 2008).

Finally, the scientific community now agrees that, once an effective preventive biological composition or vaccine against SIV 239, is discovered in the macaque, it should in all probability be successfully adaptable to humans to protect them from AIDS.

Despite constant research efforts of the scientific community, preventive and therapeutic efficient strategies remain awaited to combat the worldwide AIDS pandemic.

Various bacteria have been described to have interesting adjuvanticity and immunomodulating properties upon administration to subjects. In particular, lactic acid bacteria have been reported to promote a tolerance effect on the immune system.

For example, WO 2006/123230 published on 23 Nov. 2006 in the name of Stallergenes S.A., describes the use of a bacterium selected from Bifidobacteria and lactic acid bacteria as an adjuvant in an immunogenic composition capable of inducing antigen-specific tolerance upon sublingual, perlingual or oral administration to a subject. The immunogenic composition is proposed to be used for treating allergies, auto-immune diseases or for preventing graft rejections.

Yet for example, WO 2009/093900 published on 30 Jul. 2009 in the name of Stichting Top Institute Food and Nutrition, describes a tolerogenic composition containing a substantial amount of lactic acid bacteria in the mid-log phase. This composition induces a non antigen-specific immune tolerance when administered to a subject. The composition is proposed to be used for preventing, delaying and/or treating conditions or diseases associated with inflammatory responses that can lead to tissue damage such as allergies, autoimmune diseases, and inflammatory diseases of the intestine.

SUMMARY OF THE INVENTION

The Inventors were able to show that, surprisingly, original pharmaceutical compositions as described in the Examples below induced an efficient antigen-specific immune protection against SIV in macaques. Moreover, when said SIV-specific immune protection was induced, the Inventors showed that it prevented SIV replication/dissemination and the subsequent establishment of the infection in vivo.

Indeed, the Inventors have surprisingly shown that upon administering a pharmaceutical composition as disclosed here either mucosally or by the intradermal or intraepithelial route, virus replication was significantly inhibited, or even abrogated or prevented.

Actually, the Inventors could observe for the first time that a non-cytotoxic CD8+ T cell response suppressed the early activation of SIV antigen-presenting CD4+ T cells in macaques. Thus, without wishing to be bound by theory, the pharmaceutical compositions according to the present invention induce an unexpected new type of virus-specific immunotolerance upon mucosal or intradermal or intraepithelial administration to subjects. This immunotolerance appears to be a HIV Gag and/or Pol antigen-specific suppressive CD8+ T cell-induced immunotolerance (also named herein "Ts" immunotolerance for "T suppressive" immunotolerance), which is MHC (for "Major Histocompatibility Complex")-Ib/E-restricted and non-cytotoxic.

In the light of the results reported herein, it is provided by the present invention a novel pharmaceutical composition capable of achieving a "Ts" immunotolerance as defined above for preventing and/or treating an HIV disease in humans.

An object of the present invention is thus to provide a pharmaceutical composition comprising a mixture of an antigen and a non-pathogenic living bacterium, wherein, preferably, said antigen is particulate and/or it has one or more epitopes from HIV Gag and/or Pol proteins, and wherein said bacterium is preferably *Lactobacillus plantarum*.

It is another object of the present invention to provide a pharmaceutical composition as described herein, for use as a vaccine.

Another object of the present invention is to provide a method for preventing and/or treating an HIV disease in a human in need thereof, comprising at least the step of mucosally (preferably orally) or intradermally or intraepithelially administering an effective amount of a pharmaceutical composition as mentioned above to said human.

Yet another object of the present invention is to provide a method for protecting a human against HIV, comprising at least the step of mucosally (preferably orally) or intradermally or intraepithelially administering an effective amount of a pharmaceutical composition as mentioned above to said human.

Yet another object of the present invention is to provide a method for protecting a human from HIV seroconversion, comprising at least the step of mucosally (preferably orally) or intradermally or intraepithelially administering an effective amount of a pharmaceutical composition as mentioned above to said human.

Yet another object of the present invention is to provide a pharmaceutical kit for preventing and/or treating an HIV disease in a human in need thereof, comprising:

in a first container, an antigen; and in a second container, a non-pathogenic bacterium, wherein said antigen and said bacterium are in pharmaceutically acceptable carriers for mucosal or intradermal or intraepithelial administration, wherein preferably said antigen is particulate and/or it has one or more epitopes from HIV Gag and/or Pol proteins, and wherein said bacterium is preferably *Lactobacillus plantarum*.

BRIEF DESCRIPTION OF THE DRAWINGS

The present invention is illustrated by the following figures to which reference is made in the non-limiting examples below.

DETAILED DESCRIPTION OF THE INVENTION

Figure 1:
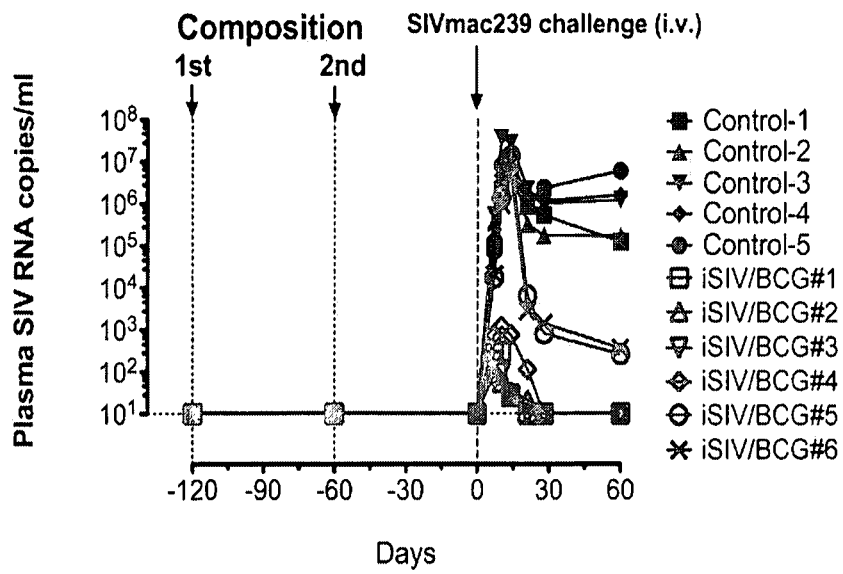
FIG. 1: Intravenous (i.v.) SIVmac239 challenge of rhesus macaques pretreated with an intravaginal iSIV/BCG.

The present invention is directed to a pharmaceutical composition comprising a mixture of an antigen and a non-pathogenic living bacterium.

The Antigen

Due to the great variability in the HIV genome, which results from mutation, recombination, insertion and/or deletion, HIV has been classified in groups, subgroups, types, subtypes and genotypes. There are two major HIV groups (HIV-1 and HIV-2) and many subgroups because the HIV genome mutates constantly. The major difference between the groups and subgroups is associated with the viral envelope. HIV-1 is classified into a main subgroup (M), said subgroup M being divided into nine subtypes (clades or subtypes) designed A through J (Hu et al., JAMA 275:210-216, 1996; Korber et al., Science 280:1868-1871, 1998), and a 10th outlier subgroup (O). Many other subgroups resulting from in vivo recombinations of the previous ones also exist (Papathanasopoulos M A, et al. Virus Genes 2003, 26:151-163). Preferably, the HIV virus is HIV-1 or HIV-2, including all known and so far unknown clades thereof. Yet preferably, it is HIV-1.

In the context of the present invention, an "antigen" is from HIV origin, which means that it is related to a specific HIV group, subgroup, type, subtype or to a combination of several subtypes. Preferably, said HIV antigen is a HIV-1 or HIV-2 antigen.

Said antigen is non-infectious.

It was suspected for a long time by the scientific community that the activation of $CD4^+$ T cells, the principal target of both HIV-1 and SIV, contributed directly to viral replication (Andrieu and Lu, 1995; Korin and Zack, 1999). However, it was only recently that the interplay between $CD4^+$ T cell activation and the successive steps of the SIV or HIV infectious process was clarified. In quiescent $CD4^+$ T cells, virus penetration was followed within 2 hours post entry by the presentation at the plasma membrane of Gag and Pol protein-derived epitopes of incoming virions while Env and Nef proteins needed de novo synthesis (Sacha et al., 2007). However, the subsequent phases of the infectious process, i.e., reverse transcription followed by virus integration, developed very inefficiently in quiescent cells (Vatakis et al., 2009a and 2009b). In contrast, when CD4+ T cells were activated before or within the 48 hours following the presentation of Gag and Pol epitopes at the plasma membrane, HIV/SIV reverse transcription and DNA integration were extremely active which allowed very efficient virus replication and release (Vatakis et al., 2009a and 2009b).

Hence, the Inventors postulated that specifically blocking in vivo the early development of HIV/SIV Gag or Pol-specific $CD4^+$ T-cell activation after HIV/SIV exposure will result in the prevention of active viral replication.

Bearing this in mind, in order to induce the suppression of the activation of HIV Gag and/or Pol antigen-presenting $CD4^+$ T cells, and in turn to prevent in vivo HIV replication and dissemination in virus-exposed humans, the pharmaceutical composition of the present invention comprises an HIV antigen that preferably has one or more epitopes from HIV Gag and/or Pol proteins. Such an antigen advantageously either contains or is derived from HIV Gag and/or Pol.

The terms "an antigen containing, or derived from, Gag and/or Pol of a HIV virus" thus mean an HIV antigen:
that comprises at least Gag and/or Pol (as an "antigen containing Gag and/or Pol"); or
that comprises one or more proteins encoded by GAG such as the capsid protein (p24) and the matrix protein (p17), and/or one or more proteins encoded by POL such as the integrase, the reverse transcriptase and the protease (as an "antigen derived from Gag and/or Pol"); or
that comprises one or more epitopes from those proteins (also as an "antigen derived from Gag and/or Pol").

In particular, any other viral proteins or epitopes thereof selected in the group consisting of ENV, VIF, VPR, VPU for HIV-1, VPX for HIV-2, REV, NEF, TAT, and the like, are not essential components of the antigen comprised in the pharmaceutical composition disclosed here. Anyone of these proteins, if present, is only an optional component of the antigen to be used in the pharmaceutical composition disclosed herein.

The antigen is preferably a particulate antigen. This means that it is preferably selected from virus particles, recombinant virus particles, virus-like particles, Gag and/or Pol-expressing recombinant bacteria or fungi, polymeric microparticles presenting on their surface one or more viral proteins or peptides or epitopes (containing or derived from HIV Gag and/or Pol). Preferably, one or more epitopes from Gag and/or Pol are produced by or expressed by or contained in said antigen. When recombinant virus particles or virus particles or Gag and/or Pol-expressing recombinant bacteria or fungi are used, these are preferably inactivated microorganisms.

The antigen may be a virus particle, a recombinant virus particle, a virus-like particle or a Gag and/or Pol-expressing recombinant bacterium or fungus. It also may be one or more viral proteins or peptides (containing or derived from HIV Gag and/or Pol), recombinant or not, either in the form of conjugates or of concatemers. The antigen is then viral nucleic acid independent, that is to say it is non viral DNA- or non viral RNA-dependent.

The antigen may result from the expression of a viral nucleic acid sequence advantageously contained into an appropriate recombinant microorganism.

If the antigen contained into the pharmaceutical composition of the present invention is a Gag and/or Pol-expressing recombinant bacterium, then said recombinant bacterium is preferably different from the non-pathogenic living bacterium that is also comprised in the composition.

When the antigen in the pharmaceutical composition according to the present invention is one or more viral proteins or peptides (containing or derived from HIV Gag and/or Pol), it is preferably under a particulate form. In practice, appropriate particulate antigens may be produced by living microorganisms such as yeasts, in the same manner as for recombinant DNA hepatitis B vaccines wherein the expressed HBsAg polypeptide self-assembles into immunogenic spherical particles closely resembling the natural 22-nm particles found in the serum of patients with chronic HBV infection (Plotkin et al., 2008).

Alternatively, when the antigen in the pharmaceutical composition according to the present invention is one or more viral proteins or peptides (containing or derived from HIV Gag and/or Pol), it is in the form of conjugates. In such an embodiment, as it is well known in the art, proteins or peptides of interest are convalently conjugated to an appropriate carrier. Conventional carriers that are commercially available are inter alia proteins such as the KLH (Keyhole Limpet Hemocyanin) protein, the BSA (Bovine serum Albumin) protein, the OVA (ovalbumin) protein, and the like (which can preferably be safely administrable orally to humans). Methods for producing appropriate conjugates are familiar to a person skilled in the art.

Yet alternatively, when the antigen in the pharmaceutical composition according to the present invention is one or more viral proteins or peptides (containing or derived from HIV Gag and/or Pol), it is in the form of concatemers. As it is well known in the art, concatemers are made of multiple copies of proteins or peptides of interest that are physically linked together in one macromolecule. In concatemers, a copy of the protein or peptide of interest can be linked to another either directly or they can be separated by a synthetic arm. A concatemer thus comprises at least two copies, preferably up to 10 copies or more, of the protein or peptide of interest. Methods for producing appropriate concatemers belong to the general knowledge of a person skilled in the art.

As used herein, a "virus-like particle" (VLP) means a particle that closely resemble mature virions, but that does not contain viral genomic material of said virus. More precisely, VLPs, which are also called pseudo-virions, represent subunit structures composed of multiple copies of a viral capsid and/or other viral proteins. These viral proteins are capable to self-assemble into VLPs of defined spherical symmetry in vivo. These VLPs do not comprise any nucleic acid molecules coding for virus proteins, and more precisely do not contain any nucleic acid molecules. Therefore, VLPs are non-replicative and non-infectious in nature, which make them safe for administration in the form of a pharmaceutical composition. Methods for producing VLPs are well known from one of skill in the art (see, e.g., Liew et al., 2010; Plummer and Manchester, 2010). Non-limiting examples of appropriate methods for producing VLPs are described in U.S. Pat. No. 5,919,458, EP 386882, WO 91/07425, U.S. Pat. No. 5,861,282 and WO 91/05864 disclosing HIV VLPs (pseudovirions) which do not comprise HIV genome nor any nucleic acid molecule.

As used herein, "a recombinant virus particle" means a virus particle which contains, or which exposed at its surface, proteins from different viruses. Besides, a recombinant virus particle can also mean a bacterium or another host cell which contains, which produces or which exposed at its surface, one or more viral proteins or peptides or epitopes containing or derived from HIV Gag and/or Pol.

Actually, most of the recombinant virus particles are virus particles in which part of original structural proteins (i.e., mainly envelope proteins and core proteins) is replaced by counterpart proteins from another virus. As an example, the envelope proteins can be exchanged. In such a case, recombinant virus particles contain a "chimeric" genome consisting in genome of a virus having the sequence encoding envelope proteins exchanged with sequence coding for envelope proteins from another virus. Most of the recombinant virus particles are replicative and infectious.

As used herein, a recombinant virus comprising proteins from another virus means that the recombinant virus particle contains one or more viral proteins or peptides or epitopes containing or derived from HIV Gag and/or Pol, either internally or present at its surface. Non-limiting examples of methods for producing recombinant virus particles are described for:

Alphavirus: in WO 02/053757 disclosing a recombinant alphavirus expressing HIV (ENV protein)

Retrovirus: in EP 1499736 disclosing lentiviral vectors expressing chimeric glycoproteins.

Adenovirus (such as type 5, 7, or 35): in US 2007/077257, US 2007/054395, JP 2007037402, WO 2006/120034, US 2004/253210, US 2004/170647, US 2005/070017, US 2003/228329, US 2004/101957, US 2003/219458, US 2004/009936, US 2004/028652, WO 03/050238, WO 03/038057, WO 03/020893, WO 02/31168, WO 02/22080, WO 01/02607, and U.S. Pat. No. 6,716,823 which disclose recombinant adenovirus expressing HIV proteins.

Pox virus (canarypox, vaccinia, vaccinia Ankara, and fowlpox virus): in U.S. Pat. No. 5,766,598, EP 0592546, US 2007/048861, US 2006/188961, US 2006/134133, EP 1789438, WO 2005/017208, WO 2004/035006, US 2004/146528, JP 2003321391, EP 1378516, WO 95/07099, JP 7170982, DE 4141741, EP 0449116, JP 1148183, JP 1085072, EP 0592546, EP 0243029, US 2005/287162, JP 2004105187, JP 2004089185, WO 03/095656, EP 0592546, WO 96/40880, U.S. Pat. No. 6,136,318, U.S. Pat. No. 5,670,367 which disclose recombinant pox virus expressing viral proteins including HIV proteins.

Bacteria which contain, which produce or which expose at their surface, at least one protein from a virus: in U.S. Pat. No. 7,189,402 and WO 96/11708 which disclose Salmonella or E. coli expressing HIV glycoproteins (i.e., envelope proteins).

Preferably, a recombinant virus particle corresponds to a poxvirus, which pox virus is preferably selected in the group comprising canarypox (e.g., ALVAC viral vectors such as the one disclosed in patent U.S. Pat. No. 5,766,598 and EP 0592546), vaccinia (e.g., the vaccinia virus disclosed in International patent application WO 95/07099), vaccinia Ankara (e.g., NYVAC viral vectors such as the one disclosed in patent application EP 1789438), and fowlpox virus (e.g., TROVAC viral vectors such as the one disclosed in International patent application WO 03/095656).

More preferably, said poxvirus is a canarypoxvirus. As an example of recombinant virus particle corresponding to canarypox virus and expressing HIV peptide/protein, one can cite the ALVAC viral vectors disclosed in patent U.S. Pat. No. 5,766,598, (incorporated herein by reference from column 6, line 18 to column 82, line 36), which ALVAC vectors express as an example HIV-1 gp120, HIV-1 gp160, non cleavable secreted form of HIV-1 env, HIV-1 gp120 anchored with a transmembrane sequence, HIV-1 gag/pol, HIV-1 gag/pol and env (gp120), HIV-1 gag/pol and env (gp160), and HIV-1 gag/pol and env (gp120 with transmembrane anchor). Preferably, said ALVAC vector express HIV-1 gag/pol and env (gp120), and most preferably said ALVAC vector is ALVAC vCP1521.

A "virus particle" is preferably an SIV or a HIV particle such as an SIV or a HIV virus particle that may contain a mutated viral genome (e.g., by nucleic acid mutation, substitution or insertion) resulting in the production of non-infectious virus particles.

Virus particles containing a mutated viral genome are disclosed in U.S. Pat. Nos. 7,229,625, 6,121,021, 6,923,970, 6,544,527, 6,451,322, and 6,080,408.

Advantageously, and to have virus particles or recombinant virus particles safe for administration to a human, said virus particles or recombinant virus particles are inactivated before being administered. Such inactivation may be necessary for recombinant virus particles, even for non-replicative ones.

As used herein "an inactivated virus particle", said virus particle being recombinant or not, means a viral particle, which is no longer infectious and, preferably, no longer replicative.

Methods for inactivation of viral particles or recombinant virus particles are well known from one of skill in the art. Non-limiting examples of viral inactivation include chemical inactivation such as formalin, taurine chloramine, formaldehyde, paraformaldehyde, propiolactene, beta-propiolactone (REMUNE) or aldrithiol-2 (AT-2, see U.S. Pat. No. 6,001,155) treatment, thermal inactivation, physical inactivation such as U.V or gamma irradiation or microwave exposure, and combinations thereof. For a reference for HIV inactivation, see RAVIV et al. (*J. Virol.*, vol. 79(19), p: 12394-12400, 2005).

According to an embodiment, said inactivation is a chemical inactivation selected in the group comprising formalin, taurine chloramine, formaldehyde, paraformaldehyde, propiolactene, beta-propiolactone (REMUNE) or aldrithiol-2 inactivation.

Alternatively or additionally, said inactivation is a thermal inactivation. Such inactivation is well known from the skilled person and, as an example of such method, one can cite the one disclosed in the examples. Indeed, the Inventors have surprisingly established in macaques that chemically (i.e., AT-2) and/or thermally inactivated virus induces a protective immunotolerance when associated to a non-pathogenic living bacterium.

Advantageously, for the purposes of administration to humans, virus particles are at least inactivated twice, typically using at least two methods of inactivation mentioned above.

Preferably, as yet mentioned above, the virus particles (recombinant or not, VLPs or not) that are used as antigens in the pharmaceutical compositions of the present invention, are not nucleic acid (i.e., DNA or RNA) dependent, which means that the virus particles do not contain any viral DNA or RNA, or if they contain DNA or RNA, it has no role in the immunogenicity.

Alternatively, polymeric microparticles (under the form of microcapsules, microspheres, and the like) of various structures and presenting on their surface one or more viral proteins or peptides or epitopes containing or derived from HIV Gag and/or Pol, may be used as antigens in the pharmaceutical compositions according to the present invention. Such microparticles may be made of appropriate biological or chemical polymers, such as methacrylated dextran, methacrylated poly(ethyleneglycol) and/or gelatin, onto which the HIV virus or viral proteins or peptides or epitopes containing or derived from HIV Gag and/or Pol can adhere. Examples of polymeric microparticles can be found in the literature (for example, in Wei Li Lee et al. (2010), Sandri et al. (2007), Goldberg et al. (2003), Delie F. (1998), Ponchel et al. (1998), Mathiowitz et al. (1997), Fasano et al. (1997), Chickering et al. (1997)).

In a preferred embodiment, the antigen in an HIV-1 pharmaceutical composition according to the present invention is one or more viral particles capable of expressing one or more viral proteins or peptides or epitopes containing or derived from HIV-1 Gag and/or Pol. Alternatively, the antigen in an HIV-1 pharmaceutical composition according to the present invention is one or more polymeric microparticles presenting on their surface one or more viral proteins or peptides or epitopes containing or derived from HIV-1 Gag and/or Pol.

Preferably, the antigen to be used in the pharmaceutical composition according to the present invention is at least about 110 kDa in size. It is preferably at least about 120, 130, 140, 150, 160, 170, 180, 190, 200 kDa or even more, in size.

An effective amount of the viral antigen to be used in the context of the invention can easily be determined by the skilled person, using the common general knowledge and in the light of the Examples disclosed hereafter, in connection with SIV or HIV virus.

As an example, when said antigen is a particulate antigen and is more specifically a virus particle, the amount of virus particles is from about $10^6$ to about $10^{12}$ per ml of said mixture.

The Non-Pathogenic Bacterium

As shown by the Inventors with SIV in macaques, when administered by the mucosal or the intradermal or the intraepithelial route together with an appropriate antigen as defined above, the non-pathogenic living bacterium comprised in the pharmaceutical composition is capable of inducing and preferably maintaining a state of immunotolerance to the above-mentioned antigen. In humans, this makes it possible to prevent and/or treat an HIV disease.

Said bacterium can thus be regarded as a particular adjuvant which can herein be designated as a "tolerogenic adjuvant" or a "tolerogenic carrier" or a "tolerogenic vehicle" or a "carrier of tolerance" or a "carrier of tolerization" or a "vehicle for tolerance", these terms being synonymous.

Preferably, all these equivalent terms refer to a non-pathogenic living bacterium that is used in combination with an HIV antigen as defined above in order to achieve a specific immune protection (preferably, immunotolerance) to the antigen, thereby preventing and/or treating an HIV disease in humans.

More preferably, a "tolerogenic vehicle" is a non-pathogenic living bacterium that is administered in admixture with an HIV antigen as defined above, in order to achieve one or more, preferably 2 or more, yet preferably 3 or more, of the following immunoprotecting effects:

1) A "tolerogenic vehicle" does not induce significant production of systemic HIV antigen-specific antibodies:
In particular, no significant production of systemic anti-HIV IgM and/or IgG antibodies is observed. For example, there is no significant systemic humoral response that is to say either no specific detectable systemic antibody response can be detected by classical clinical laboratory methods such as ELISA, or if systemic antibodies are detected, they are not protective against HIV virus infection.

2) A "tolerogenic vehicle" does not induce significant HIV antigen-specific proliferation of CD4+ T cells:
In particular, no significant proliferation of HIV antigen-specific CD4 cells is observed upon in vitro HIV antigen stimulation as measured by standard assays such as that described in the accompanying examples.

3) A "tolerogenic vehicle" does not induce significant production of gamma-interferon by CD8+ T cells upon in vitro HIV antigen stimulation:
In particular, the level of gamma interferon secretion by CD8+ T cells which is observed upon in vitro HIV antigen stimulation is below the threshold level for an ELIspot assay.

4) A "tolerogenic vehicle" induces a significant CD8+ T cell response suppressing the activation of HIV antigen-presenting CD4+ T cells:

In particular, this response can be determined by an in vitro test measuring the level of inhibition of viral replication by CD8+ T cells (indicating a "significant" CD8+ T cell response) as shown in the accompanying examples. These CD8+ T cells are also called CD8+ "regulatory" T-cells. Yet in particular, this response is non-cytotoxic given that, e.g., it does not induce significant production of gamma-interferon. Yet in particular, this response is MHC-Ib/E-restricted. Yet in particular, TCRαβ appear to be involved in the CD8+ T cell response suppressing viral replication. Yet in particular, this response suppresses the activation of HIV antigen-presenting CD4+ T cells compared to the same cell population depleted of CD8+ T cells. Preferably, said response suppresses the early activation of HIV antigen-presenting CD4+ T cells, wherein said "early" activation is measured by the Ki67+ marker (Scholzen and Gerdes. J. Cell Physiol. 182, 311-322 (March 2000)).

By the terms "does not induce" as used above in 1), 2) and 3), it is meant a result below the threshold level for an appropriate quantitative detecting assay, wherein said "threshold level" is a value determined in the assay on the basis of the negative control(s): under this value, the result is a negative result. This value may vary from an assay to another and from a method of detection to another.

Advantageously, the tolerogenic vehicle is selected from living:
  non-pathogenic bacteria, especially probiotics and commensal bacteria;
  attenuated pathogenic bacteria; and
  inactivated (optionally, also previously attenuated) pathogenic bacteria.
  The tolerogenic vehicle may be recombinant or not.

"Non-pathogenic bacteria" to be used as tolerogenic vehicles in the context of the present invention do not generally induce any pathology in humans. This is the reason why they are Generally Recognized As Safe (GRAS). Of course, such bacteria have to be administrable to humans.

Preferred non-pathogenic bacteria to be used as tolerogenic vehicles are commensal bacteria. Such bacteria are well-known to the skilled artisan. Non-limiting examples include *Bacillus* sp. (e.g., *B. coagulans*), *Bifidobacterium animalis*, *Bifidobacterium breve*, *Bifidobacterium infantis*, *Bifidobacterium longum*, *Bifidobacterium bifidum*, *Bifidobacterium lactis*, *Escherichia coli*, *Lactobacillus acidophilus*, *Lactobacillus bulgaricus*, *Lactobacillus casei*, *Lactobacillus paracasei*, *Lactobacillus johnsonii*, *Lactobacillus plantarum*, *Lactobacillus reuteri*, *Lactobacillus rhamnosus*, *Lactobacillus brevis*, *Lactobacillus gasseri*, *Lactobacillus salivarius*, *Lactococcus lactis*, *Streptococcus thermophilus*, and the like.

A "commensal bacterium" for use as a tolerogenic vehicle in the context of the present invention is advantageously a lactic acid bacterium or a bifidobacterium which is more particularly selected in the list above, including also combinations thereof. A preferred commensal bacterium is *Lactobacillus* sp., and more preferably *Lactobacillus plantarum*. The Examples reported below show for the first time that *Lactobacillus plantarum* is a tolerogenic vehicle, leading to viral immunotolerance when administered together with an antigen as defined above.

Advantageously, a combination of non-pathogenic bacteria, such as two or more commensal bacteria, may be used as the tolerogenic vehicle.

As used herein, the terms "pathogenic bacteria" refer to bacteria inducing pathologies in humans. Such bacteria are well known from the skilled person and include inter alia *Listeria* species (e.g., *Listeria monocytogenes*), *Corynebacterium* species, *Mycobacterium* species, *Rhococcus* species, *Eubacteria* species, *Bortadella* species and *Nocardia* species. Preferably, a pathogenic bacterium is selected among *Mycobacterium* species, and is more preferably *Mycobacterium bovis*.

As used herein, "attenuated pathogenic bacteria" are pathogenic bacteria which are less virulent compared to their wild-type counterpart because of one or several mutations or of one or more attenuation treatments (e.g., chemical treatment and/or successive passages on specific media). Such attenuated pathogenic bacteria are well known from the one of skill in the art. Non-limiting examples of attenuated pathogenic bacteria include attenuated *Salmonella typhimurium* and *Mycobacteria* with a preference for attenuated *Mycobacteria*. As an example of attenuated *Mycobacteria*, one can cite the "Bacille de Calmette Guerin", also known as "BCG", and, more especially, among others, the six widely used BCG strains—the evolutionarily early strain BCG Japanese, the two evolutionarily late strains in DU2 Group III (BCG Danish and Glaxo), and the three evolutionarily late strains in DU2 Group IV (BCG Connaught, Pasteur, and Tice). As another example of attenuated *Mycobacteria*, one can also cite recombinant BCG such as the strain rBCG30 disclosed in HOFT et al. (2008), the recombinant BCG disclosed in WANG et al (2008), and also the recombinant BCG disclosed in International patent applications WO 2005/111205 and WO 02/102409, and disclosed in patents U.S. Pat. No. 7,122,195 and U.S. Pat. No. 6,261,568.

Advantageously, instead of or additionally to being attenuated, pathogenic bacteria may be inactivated to be used as tolerogenic vehicles in the context of the present invention, but attenuated pathogenic bacteria may also be used after having been inactivated.

"Inactivated pathogenic bacteria" are well known from the one of skill in the art. Methods of preparation of such inactivated pathogenic bacteria form part of the common general knowledge in the art. As an example of such methods, one can cite phage mediated lysis, chemical inactivation such as formalin treatment (see U.S. Pat. No. 7,393,541), thermal inactivation, physical inactivation such as lyophilisation (e.g., Extended Freeze Drying) or U.V or gamma irradiation (see WO 2008/128065) or microwave exposure, and combinations thereof.

Preferably, said tolerogenic vehicle is an attenuated derivative of pathogenic bacteria like BCG. The Examples reported below show for the first time that BCG is a tolerogenic vehicle, leading to viral immunotolerance when administered together with an antigen as defined above.

When recombinant, the tolerogenic vehicle according to the present invention does not express any HIV protein or peptide or epitope.

Preferably, at least a significant amount of the living bacteria used as a tolerogenic vehicle is in the mid-log phase. More preferably, at least about 50%, 55%, 60%, 65%, 70%, 75%, 80%, 85%, 90%, 95%, or even about 100% of the total number of bacterial cells is in the mid-log phase.

An effective amount for a tolerogenic vehicle can be easily determined by the skilled person and examples of such an effective amount are disclosed hereinafter.

As an example, the amount of said bacterium in the pharmaceutical composition of the present invention is from about $10^4$ to about $10^{14}$ CFU per ml of said mixture.

The Pharmaceutical Composition

Said composition is also referred to herein as a "tolerogenic composition" or a "tolero-immunogenic composition", these terms being equivalent.

The tolerogenic vehicle and the antigen containing, or derived from, Gag and/or Pol of a HIV virus are two separate and distinct components that are contained as a mixture into the pharmaceutical composition of the present invention. This means that said tolerogenic vehicle and said antigen are present as distinct components in said composition.

Advantageously, the pharmaceutical composition of the invention does not comprise any oligonucleotide (e.g., CpG or dsRNA) as adjuvant.

Since the tolerogenic vehicle is a bacterium, a bacterium of the same genus and/or species may be separately used under a recombinant form as a source of antigen. For instance, the recombinant bacterium will contain a nucleic acid encoding the antigen placed under the control of appropriate regulatory sequences (including promoters— inducible or constitutive-), either on a nucleic acid vector contained into the cell or as an integrated nucleic acid sequence into the bacterial chromosome. Thereby, the recombinant bacterium will be able to express or produce said antigen. Thus, according to a particular embodiment, the pharmaceutical composition of the present invention incorporates a tolerogenic vehicle which is a bacterium and an antigen which is one or more viral proteins or peptides or epitopes containing or derived from HIV Gag and/or Pol, and which has been separately produced by a recombinant bacterium belonging to the same genus and/or species as the tolerogenic vehicle.

In a pharmaceutical composition according to the present invention, when said antigen is a particulate antigen and more specifically a virus particle, the ratio in said mixture of said virus particle (expressed in particles per ml of said mixture) to said bacterium (expressed in CFU per ml of said mixture) is from about 1:10 to about 1:1000, preferably from about 1:25 to about 1:750, yet preferably from about 1:50 to about 1:500, even yet preferably from about 1:75 to about 1:250, and yet further preferably about 1:100.

Administering the Pharmaceutical Composition of the Invention

It may be possible to administer the tolerogenic vehicle and the antigen either simultaneously, or separately, or sequentially.

It is thus an object of the present invention to provide a pharmaceutical kit for preventing and/or treating an HIV disease in a human in need thereof, comprising:
  in a first container, an antigen as defined above; and
  in a second container, a non-pathogenic living bacterium as defined above,
wherein said antigen and said bacterium are in pharmaceutically acceptable carriers for mucosal or intradermal or intraepithelial administration.

It is also an object of the present invention to provide products containing:
  a non-pathogenic living bacterium as a tolerogenic vehicle as defined above; and
  a particulate antigen or an antigen having one or more epitopes from HIV Gag and/or Pol proteins as defined above,
as a combined pharmaceutical composition for simultaneous, separate or sequential use in preventing and/or treating an HIV disease in a human in need thereof. Said prevention and/or treatment is(are) achieved via mucosally or intradermally or intraepithelially administering said combined pharmaceutical composition to said human. To do so, it may be possible to administer the tolerogenic vehicle and the antigen either simultaneously, or separately, or sequentially.

As an example, the non-pathogenic living bacterium may be administered orally (e.g., as an oral drug or a food supplement), whereas the antigen is administered mucosally, or intradermally or intraepithelially.

Of course, appropriate pharmaceutical vehicles may be used in order to ensure a suitable delivery of each to the expected site (e.g., a mucosal surface). The time and dose for administering each of the tolerogenic vehicle and the antigen will be easily adapted by the skilled artisan.

Preferably, the pharmaceutical composition according to the present invention is a mucosal or intradermal or intraepithelial pharmaceutical composition. Yet preferably, it is an oral pharmaceutical composition.

As used herein, a "mucosal or intradermal or intraepithelial pharmaceutical composition" is a pharmaceutical composition for mucosal or intradermal or intraepithelial administration, which means that it is formulated for such an administration.

In particular, the pharmaceutical composition may further comprise one or more appropriate pharmaceutical vehicles (or supports) for mucosal or intradermal or intraepithelial delivery of said antigen and of said bacterium.

Preferably, a "mucosal delivery" is herein selected from nasal, oral, sub-lingual, tracheal, pharyngeal, bronchial, esophageal, gastric, duodenal, intestinal, rectal, preputial and vaginal deliveries. A "mucosal delivery" is a delivery to a mucosal surface, such as nasal, oral, sub-lingual, tracheal, bronchial, pharyngeal, esophageal, gastric, and mucosae of the duodenum, small and large intestines, including the rectum, as well as preputial and vaginal mucosae. In the present context, the mucosal surface also includes the external surface of the eye, i.e., the mucosa of and that surrounding the eye. Yet preferably, the mucosal surface refers to vaginal and digestive mucosa, and more preferably to digestive mucosa. Yet preferably, the mucosal delivery is an oral delivery.

Thus, the pharmaceutical composition may also comprise one or more pharmaceutical vehicles depending on the route of administration. Those of ordinary skill in the pharmaceutical art are familiar with, or can readily ascertain, vehicles for drug delivery to a mucosal surface or for an intradermal or intraepithelial delivery. Useful references in this regard are Chien (Novel Drug delivery system, Chapters 3 through 6 and 9, Marcel Dekker, 1992), *Ullmann's Encyclopedia of Industrial Chemistry*, 6$^{th}$ *Ed.* (various editors, 1989-1998, Marcel Dekker); and *Pharmaceutical Dosage Forms and Drug Delivery Systems* (ANSEL et al., 1994, WILLIAMS & WILKINS).

Exemplary methods and routes for drug delivery useful in the invention are briefly described below.

Administration to the bronchial, bronchiolar, tracheal, nasal, oral, preputial or pharyngeal mucosa can be obtained by formulating the pharmaceutical composition as inhalable, spray and the like (e.g., nasal spray, aerosol spray or pump spray and the like), solution, gel, etc. Nebulizer devices suitable for delivery of pharmaceutical compositions to the nasal mucosa, trachea and bronchioli are well-known in the art and will therefore not be described in detail here. The pharmaceutical composition may then comprise a vehicle selected in the group comprising solutions, emulsions, microemulsions, oil-in-water emulsions, anhydrous lipids and oil-in-water emulsions, other types of emulsions.

Administration to the vaginal mucosa can be obtained by formulating the pharmaceutical composition as solution, enema, foam, suppository, vaginal tablet or topical gel. Preferred vehicles for vaginal delivery include hydrophilic and hydrophobic vehicles such as those commonly used in formulating emulsion or gel preparations (e.g., oil/water emulsion gel).

Administration to the digestive tract mucosa can be obtained by formulating the pharmaceutical composition as capsule, microcapsule. Preferred vehicles for digestive delivery correspond to capsules and microcapsules (e.g., capsules and microcapsules of pectin and/or alginate) generally given per os such as those commonly used in formulating preparations for digestive delivery (e.g., the microcapsules disclosed in International patent application WO 2007/140613). Alternatively, digestive delivery may be obtained by consuming or administering appropriate liquids and/or foodstuffs, such as beverages, yoghourts, and the like.

Intradermal or intraepithelial administration is well-known to the skilled artisan. Intradermal administration (e.g., injection) can for instance be done with needle-devices such as those disclosed in patent U.S. Pat. No. 6,933,319 and in International patent application WO 2004/101025, or with appropriate needle-free devices.

The pharmaceutical composition may further comprise at least one absorption agent. "Absorption agents" are well known from the one of skill in the art. As examples, one can cite surfactants such as polyoxyethylene derivatives of fatty acid partial esters of sorbitol anhydrides (e.g., Tween® 80, Polyoxyl 40 Stearate, Polyoxyethylene 50 Stearate, polyoxyethylene-9-lauryl ether and Octoxynol), bile salts such as sodium glycocholate, mixed micelles, enamines, nitric oxide donors (eg., S-nitroso-N-acetyl-DL-penicillamine, NOR1, NOR4-which are preferably co-administered with an NO scavenger such as carboxy-PITO or doclofenac sodium), sodium salicylate, glycerol esters of acetoacetic acid (eg., glyceryl-1,3-diacetoacetate or 1,2-isopropylideneglycerine-3-acetoacetate), cyclodextrin or beta-cyclodextrin derivatives (e g., 2-hydroxypropyl-beta-cyclodextrin and heptakis (2,6-di-O-methyl-beta-cyclodextrin)), medium-chain fatty acid such as mono- and diglycerides (eg., sodium caprate-extracts of coconut oil, Capmul), or triglycerides (eg., amylodextrin, Estaram 299, Miglyol 810), polymers such as carboxymethylcellulose, carbopol, polycarbophil, tragacanth and sodium alginate, and other absorption agents adapted for mucosal or intradermal or intraepithelial delivery. For a reference concerning general principles regarding absorption agents, which have been used with success in mucosal or intradermal or intraepithelial delivery of drugs, see Chien, Novel Drug Delivery Systems, Ch. 4 (Marcel Dekker, 1992).

The pharmaceutical composition may further comprise one or more additives (e.g., diluents, excipients, stabilizers, preservatives, and the like). See, generally, Ullmann's Encyclopedia of Industrial Chemistry, $6^{th}$ Ed. (various editors, 1989-1998, Marcel Dekker); and Pharmaceutical Dosage Forms and Drug Delivery Systems (ANSEL et al., 1994, WILLIAMS & WILKINS).

As disclosed below, appropriate dosages of the pharmaceutical composition according to the present invention to be administered to a human subject may be determined depending on one or more characteristics of said subject such as sex, age, weight, health, etc.

As an example, when the antigen is particulate and, more specifically, when it is a virus particle, a dose of about $10^8$ to about $10^{14}$ virus particles per day may be administered to said human. As another example, a dose of non-pathogenic living bacterium of about $10^6$ to about $10^{16}$ CFU per day may be administered to said human.

Applications of the Pharmaceutical Composition of the Invention

It is an object of the present invention to provide a pharmaceutical composition as described above, for use as a medicament, preferably as a vaccine.

The present invention also relates to a method for preventing and/or treating an HIV disease in a human in need thereof, comprising at least the step of mucosally or intradermally or intraepithelially administering an effective amount of a pharmaceutical composition as defined above to said human.

According to the present invention, for preventive purposes, a "human in need thereof" can be any human, preferably having at least about 2 years old. For therapeutic purposes, a "human in need thereof" is a human to be treated because he/she is suffering from an HIV disease.

An "HIV disease" refers to any HIV-related immune disorder, including AIDS as well as earlier stages of disease progression, including seroconversion (establishment of chronic infection).

The present invention further relates to a method for protecting a human against HIV, comprising at least the step of mucosally or intradermally or intraepithelially administering an effective amount of a pharmaceutical composition as defined above to said human.

In particular, such a method enables to protect a human from an HIV infection if mucosally exposed to HIV and/or from HIV replication if intravenously exposed to HIV.

The present invention yet further relates to a method for protecting a human from HIV seroconversion, comprising at least the step of mucosally or intradermally or intraepithelially administering an effective amount of a pharmaceutical composition as defined above to said human. Thereby, said human will not become seropositive and will not exhibit a significant level of HIV antibodies.

The term "vaccination" refers to the action(s) (especially, administering the pharmaceutical composition of the present invention) that is(are) taken for preventing and/or treating an HIV disease in a human. Preferably, the pharmaceutical composition of the invention is useful for inducing and, preferably, maintaining immunotolerance to an antigen containing, or derived from, Gag and/or Pol of a HIV virus in a human that is to say, in other words, for vaccinating (or "tolerizing") said human. Thus, vaccinating a human using the pharmaceutical of the present invention is regarded as a "tolerogenic vaccination" (or a "tolerization" or a "tolerisation").

If, after the mucosal or the intradermal or the intraepithelial administration of the pharmaceutical composition of the invention (i.e., after tolerogenic vaccination), immunotolerance has been successfully induced in a human, said human is considered as being "vaccinated" (or "tolerized" or "tolerant"). The response, i.e., the viral replication as evaluated by the plasma viral RNA load of a "vaccinated" human to an in vivo viral infectious challenge is reduced by at least about 50%, more preferably by at least about 70%, yet more preferably by at least about 75% or 80% or 85% or 90% or 95% or 98% or 99%, or even more (99.5%, 99.8%, 99.9%, 100%), relative to the plasma viral RNA load of a control human to which either the antigen alone or the antigen associated with a standard adjuvant (as defined above) or no pharmaceutical composition or a placebo, was administered.

According to the present invention, a tolerogenic vaccination may comprise one or several consecutive administrations of the pharmaceutical composition. Preferably, the tolerogenic vaccination may comprise at least two or more consecutive administrations (i.e., vaccinations), and more preferably more than two consecutive administrations of said composition.

Advantageously, the interval between consecutive tolerogenic vaccinations is comprised between 1 minute and 3 months, preferably between 15 minutes and 2 months.

Yet advantageously, the tolerogenic vaccinations of the invention may also include recall tolerogenic vaccinations one or several years after the first mucosal or intradermal or intraepithelial tolerogenic vaccination (e.g., 1 to 10 years).

The new tolerogenic vaccinations following the first mucosal or intradermal or intraepithelial tolerogenic vaccination may be selected from mucosal, intradermal and intraepithelial tolerogenic vaccinations. Noticeably, if the new tolerogenic vaccinations are intraepithelial or intradermal injections, then a specific systemic humoral and/or a cytotoxic (gamma interferon producing-) response may be detectable but having no role on the prevention or treatment of the disease.

According to the present invention, an effective amount of the pharmaceutical composition is administered to a human in need thereof. The terms "effective amount" mean a sufficient amount to achieve the desired biological effect, which is here a curative or protective effect (in other words, an immunoprotecting effect) through induction of an immunotolerance, preferably a "Ts" immunotolerance. It is understood that the effective dosage will be dependent upon the age, sex, health, and weight of the subject to be treated, the kind of concurrent treatment, if any, the frequency of treatment, and the nature of the expected effect. The ranges of effective doses provided below are not intended to limit the invention and represent preferred dose ranges. However, the preferred dosage can be adapted to the subject, as it is understood and determinable by the one of skill in the art, without undue experimentation. See, e.g., Ebadi, Pharmacology, Little, Brown and Co., Boston, Mass. (1985).

For instance, with respect to HIV, a typical dosage for a human adult will be from about $10^6$-$10^{12}$ HIV virus particles (i.e., VLP, recombinant or non-recombinant virus particles) per dose, with $10^8$-$10^{10}$ preferred. Of course, whatever dosage is used, it should be a safe and effective amount as determined by known methods, as also described herein.

Moreover, the one of skill in the art can also determine in the light of his/her general knowledge the effective amount of tolerogenic vehicle to be administered to a human in order to achieve the desired biological effect.

As an example, said effective amount for attenuated derivative of pathogenic bacteria (e.g., BCG) is comprised in the range of $10^4$ to $10^{12}$, preferably $10^5$ to $10^{10}$ CFU (colony forming unit), and more preferably $10^6$ to $10^8$ CFU per dose. As another example, said effective amount for attenuated derivative of pathogenic bacteria or inactivated pathogenic bacteria (e.g., BCG) is comprised in the range of 0.001 mg to 1 g, preferably 0.01 to 100 mg, and more preferably 0.1 to 10 mg per dose.

As another example, said effective amount for non-pathogenic bacteria (e.g., *Lactobacillus* sp.) is comprised in the range of about $10^6$-$10^{14}$ CFU, and more preferably about $10^{10}$-$10^{12}$ CFU per dose.

As described above, the pharmaceutical compositions of the present invention are suitable for preventing a future HIV disease in a human, or for treating a human yet suffering from an HIV disease.

For therapeutic purposes, the "antigen containing, or derived from, Gag and/or Pol of a HIV virus" as defined above may be autologous, that is to say it may be derived from the HIV virus infecting the human to be treated. In such a case, for example, the HIV virus may be isolated from the human, then it may be cultured and inactivated (preferably at least inactivated twice), to be finally associated with a tolerogenic vehicle so as to obtain a pharmaceutical composition as described above.

Yet for example, the pharmaceutical composition comprising an autologous or non-autologous antigen containing or derived from HIV Gag and/or Pol may be administered to the human during a conventional antiviral treatment which would have first led to an undetectable viral load. The conventional antiviral treatment may then be stopped after one or more tolerogenic vaccinations using the pharmaceutical composition, provided appropriate ex vivo viral replication suppression of non-autologous acutely infected CD4 cells is achieved by autologous virus-specific CD8 cells, or provided appropriate suppression of CD4 T cell activation induced by CD8 T cells is achieved.

In particular, for therapeutic purposes, the pharmaceutical composition may be administered once only during the life of the human to be treated. Alternatively, it may be administered twice or more times during the life of the human to be treated, on the same day or on different days separated by a period ranging for example from about 1 day to about 1 year, or more. More particularly, it may be administered every day or periodically, for periods ranging for example from about 1 day to about 1 year, or more. If necessary, the pharmaceutical composition may be administered all along the life of the human to be treated.

The present invention further provides an in vitro method for determining whether a human is protected against a HIV virus, comprising:
a) isolating peripheral blood CD8 T cells from a blood sample of said vaccinated human;
b) cultivating under appropriate conditions:
   (i) said isolated CD8 T cells with allogenic or autologous CD4+ T cells which were in vitro acutely infected by a viral strain equivalent to said HIV virus; and
   (ii) said in vitro acutely infected allogenic or autologous CD4+ T cells;
c) recovering the culture supernatants;
d) measuring the viral load in said supernatants; and
e) determining whether said human is protected against said HIV virus, or not.

By "a viral strain equivalent to a HIV virus to be tested", it is meant that said viral strain originates from a wild virus and has essential characteristics similar to those of the HIV virus to be tested (for example, one can cite the viral strain HTLVIIIB originating from an individual HIV-1: HTLVIIIB can be considered as "a viral strain equivalent to" HIV-1). Preferably, said viral strain will originate from a wild virus which is the HIV virus to be tested. Said viral strain thus represents an appropriate model for studies involving a HIV virus, especially a wild HIV virus. The viral strain is of course well-adapted for such studies, especially in terms of safety.

All the steps above can be performed using standard techniques that are well-known from the person skilled in the art. In particular, the appropriate culture conditions for step b) are part of the general knowledge in the field of the invention (such as the conventional methods described in the Examples below).

The viral load can be measured in step d) by conventional methods such as those described in the Examples below.

The viral load in the supernatant recovered from the culture of said in vitro acutely infected allogenic or autologous CD4+ T cells according to sub-step b)(ii) will be used as a reference for the determination in step e). One will advantageously calculate the "percent suppression (%)" or "suppressive ratio" or "antiviral effect" by, e.g., comparing the geometric mean of viral concentration in the supernatants from duplicate (or triplicate or quadruplicate or more)

wells containing only cells from the in vitro acutely infected allogenic or autologous CD4+ T cells with the geometric mean of viral concentration in the supernatants from duplicate (or triplicate or quadruplicate or more) wells containing CD8 T cells, and cells from the in vitro acutely infected allogenic or autologous CD4+ T cells.

Then, said determination in step e) is preferably performed as follows:

If the suppressive ratio is higher than about 100, one can conclude that said human is protected. Typically, this will be the case if a HIV-non infected human has been administered an efficient preventive antiviral treatment or if a HIV-infected human has been administered an efficient therapeutic treatment, said efficient preventive or therapeutic treatment comprising preferably a pharmaceutical composition according to the present invention, and it will thus not be necessary to further administer any preventive or therapeutic treatment to the human, as long as it remains protected.

If the suppressive ratio is lower than about 100, one can conclude that said human is not protected against said virus. Then, the human, either a HIV-non infected human or a HIV-infected human, will advantageously be administered a preventive or therapeutic treatment comprising a pharmaceutical composition according to the present invention, respectively, and the in vitro method above will be performed once or more at appropriate time intervals to make sure the human become protected.

Also, the present invention provides a kit for in vitro determining whether a human is protected against a HIV virus, comprising allogenic or autologous CD4+ T cells that can be infected by a viral strain, said viral strain being, as defined above, equivalent to said HIV virus to be tested. The kit may also include an adequate viral strain in appropriate concentration to infect the above-mentioned allogenic or autologous CD4+ T cells and/or appropriate reagents and/or controls and/or media (such as media for cell suspension, cell culture, cell storage, etc.). The kit of the present invention may be specific to a particular type of HIV virus, or it may be adapted to various types of virus, said types of virus being close (in particular, phylogenetically close).

The present invention can easily be adapted in order to be used for preventing and/or treating any chronic infectious diseases. Non-limiting examples of such diseases are: hepatitis B and C, human papilloma virus (HPV), EBV and other herpes viruses, tuberculosis, leprosis, leishmaniosis, etc.

Globally, each time where one or several pathogenic antigens associated with the above-mentioned infections or diseases are involved in the specific activation of CD4+ T cells which present epitopes derived from above-mentioned pathogenic proteins or peptides, the specific suppression/prevention of activation of CD4+ T cell can be raised by non-cytotoxic CD8+ T cells generated by mucosal or intraepithelial or intradermal pharmaceutical compositions associating the above-mentioned antigen(s) and a tolerogenic vehicle as described herein.

It is herein shown that viral infections and associated diseases can be prevented and/or treated in mammals/humans using pharmaceutical compositions of the present invention. Based on this teaching, it is possible to provide other pharmaceutical compositions comprising (i) tolerogenic vehicles as disclosed herein; and (ii) any antigens from viral, bacterial, fungal, protozoal or parasitic origin. Such pharmaceutical compositions are formulated for appropriate delivery (preferably, mucosal or intradermal or intraepithelial) of said tolerogenic vehicles and of said antigens. They are useful for preventing and/or treating chronic infections in mammals caused by the virus, bacteria, fungi, protozoa or parasites which the antigens are derived from. An example is a bacterial pharmaceutical composition comprising (i) a tolerogenic vehicle as described herein; and (ii) an antigen derived from *Mycobacterium tuberculosis*. This bacterial pharmaceutical composition is formulated for appropriate delivery (preferably, mucosal or intradermal or intraepithelial) of said antigen and of said tolerogenic vehicle. Of particular interest for preventing and/or treating tuberculosis in humans is such a bacterial pharmaceutical composition wherein the mycobacterial antigen is derived from the Koch's *bacillus*.

the Immune Protection Achieved by the Pharmaceutical Composition of the Invention Tolerance is the physiological capacity of the immune system to recognize antigens taken in through the mucosal system and to develop anergy generally associated with other immunological modifications to a subsequent encounter with the same antigens. Tolerance had been frequently shown to elicit mucosal sIgA permitting antibody containment of mucosal antigens without stimulating the systemic immune compartment. TGF-beta, a regulatory cytokine had also been sometime involved in the development of tolerance. The active suppression by CD25+ regulatory T cells had also been frequently suggested as a potential mechanism of mucosal tolerance (Faria and Weiner, 2005; Mestecky et al., 2007). However, none of these immunological modifications was observed in the pharmaceutical composition-induced immunotolerance described in the present invention, which is principally characterized by the activity of CD8+ T cells which suppress the activation of virus-epitope antigen-presenting CD4+ T cells, a type of immune reaction so far unrecognized and, more specifically, a completely new type of immune tolerance.

The expressions "tolerance", "immunological tolerance", "immunotolerance", "immunotolerance to a virus", "new type of virus-specific tolerance", "immunotolerance to viral antigens", "immunotolerance to viral immunogens", and "Ts" immunotolerance" are synonymous. This has been shown by the Inventors to correspond in macaques to an actively-induced strong non-cytotoxic, MHC-Ib/E-restricted CD8+ T cell response suppressing the early activation of HIV Gag and/or Pol antigen-presenting CD4+ T cells associated with an absence of proliferation of CD4+ T cells, together with a lack of gamma interferon secretion by CD8+ T cells upon inactivated SIV antigen stimulation and a lack of production of systemic anti-SIV IgM and IgG antibodies. Also, the Inventors could show that TCRγδ and Vβ8 were not involved in CD8+ T cell suppression of viral replication, suggesting that TCRαβ should play a central role in the recognition of MHC-Ib/E-peptide presentation on infected CD4+ T cells.

A "usual immune response to an antigen derived from a virus" can be observed inter alia upon vaccination with a conventional preventive vaccine composition comprising an antigen containing, or derived from, Gag and/or Pol of a HIV virus and a standard or conventional adjuvant (i.e., any form of physical, chemical or biological adjuvant aimed at stimulating and/or facilitating and/or increasing the immune response associated with the antigen, such as those described in the Chapter entitled "Adjuvants" in "Vaccines" by S. Plotkin et al). Such a "usual immune response to an antigen derived from a virus" involves humoral, cellular, or both humoral and cellular immune responses, and is conventionally characterized by:

(i) the proliferation of virus-specific CD4 cells upon specific in vitro stimulation; and/or
(ii) the induction of a specific systemic humoral response via the production of systemic antibodies against viral antigenic proteins and/or peptides; and/or
(iii) the induction of a specific cellular response associated with the production of gamma interferon by CD8 T cells, and/or
(iv) the absence of non-cytotoxic, CD8+ T cell response suppressing the activation of HIV Gag and/or Pol antigen-presenting CD4+ T cells.

By contrast, a pharmaceutical composition comprising an antigen containing, or derived from, Gag and/or Pol of a HIV virus and a tolerogenic vehicle, as provided by the present invention, generates an "immunotolerance to a virus" and, more particularly, a ""Ts" immunotolerance" which is characterized in the Examples below with respect to SIV in macaques, by:

(i) the absence of proliferation of virus-specific CD4 cells upon specific in vitro stimulation; and (ii) the absence of any significant systemic humoral response, that is to say either no specific detectable systemic antibody response can be detected by classical clinical laboratory methods such as ELISA, or if systemic antibodies are detected, they are not protective against SIV virus infection; and (iii) the absence of any cytotoxic CD8+ T cell response associated with the production of gamma interferon (e.g., detectable by ELIspot) upon adequate in vitro stimulation, or if a cytotoxic CD8 T cell response is detected, it is not protective against SIV virus infection; and (iv) as an essential feature, the actively-induced strong non-cytotoxic, non CD25 MHC-Ib/E-restricted CD8+ T cell response suppressing the early activation of SIV antigen-presenting CD4+ T cells.

As mentioned above, the pharmaceutical composition of the present invention comprises a tolerogenic vehicle and an antigen containing, or derived from, Gag and/or Pol of a HIV virus. Actually, a tolerogenic vehicle combined to the viral antigen induces a state of virus-specific immunotolerance in a human, instead of eliciting a usual immune response as defined above. Thus, the antigen administered by the mucosal or the intradermal or the intraepithelial route, alone or associated with a standard adjuvant is generally capable of eliciting a usual immune response, excepting when it is associated with a tolerogenic vehicle as in the pharmaceutical composition of the present invention. Under these specific circumstances, the association tolerogenic vehicle/antigen in the pharmaceutical composition of the present invention induces an immunotolerance as defined above. This means that immunotolerance can only be achieved upon administering (by the mucosal or the intradermal or the intraepithelial route) an appropriate mixture of a tolerogenic vehicle and an antigen containing, or derived from, Gag and/or Pol of a HIV virus. If one is administered to a human in the absence of the other, the human will not be "vaccinated" or "tolerized".

As shown in the Examples below (using SIV in the macaque model), the immunotolerance (also called "Ts" immunotolerance) induced or achieved upon administering the pharmaceutical composition according to the present invention is characterized by a CD8+ T cell response (in particular, non-cytotoxic and/or MHC-Ib/E-restricted) that suppresses the activation (especially the early activation) of SIV Gag and/or Pol antigen-presenting CD4+ T cells; and advantageously by one or more of: 1) an absence of proliferation of CD4+ T cells; 2) a lack of significant gamma interferon secretion by CD8+ T cells upon SIV antigen stimulation; and 3) a lack of significant production of systemic anti-SIV IgM and IgG antibodies.

By the terms "lack of significant gamma interferon secretion by CD8+ T cells upon HIV or SIV antigen stimulation", it is meant herein that the level of gamma interferon secretion by CD8+ T cells which is observed upon HIV or SIV antigen stimulation is zero or weak. A "weak" gamma interferon secretion by CD8+ T cells upon HIV or SIV antigen stimulation is typically less than about 80 SFCs per $2\times10^5$ PBMCs.

By the terms "lack of significant production of systemic anti-HIV or anti-SIV IgM and IgG antibodies", it is meant herein that the level of production of systemic anti-HIV or anti-SIV IgM and IgG antibodies which is observed is zero or weak. A "weak" production of systemic anti-HIV or anti-SIV antibodies is typically a titer of anti-HIV or anti-SIV of about 300 or less.

Thus, the pharmaceutical composition according to the present invention induces and preferably maintains an antigen-specific immune protection against HIV in a human, wherein said immune protection is preferably characterized by:

the reduction and preferably the suppression of an HIV viral load in said human compared to appropriate experimental controls; and/or CD8+ T cells that suppress the activation of HIV Gag and/or Pol antigen-presenting CD4+ T cells in said human compared to appropriate experimental controls.

Advantageously, said immune protection is determined in said human by in vitro detecting the presence or the activity of CD8+ regulatory T-cells from said human. Such detection may be performed by standard in vitro techniques, such as those described in the Examples below.

All patents, patent applications and publications referred to above are hereby incorporated by reference.

EXAMPLES

Part A—General Materials & Methods

A-I Animals. Colony-bred Chinese rhesus macaques (*Macaca mulatta*) were housed in accordance with the regulations of the National Institutes of Health 'Guide for the Care and Use of Laboratory Animals'. All animals were in good health, 2-4 years old, weighed 4-6 kg and were seronegative for SIV, SRV, simian T cells lymphotropic virus 1, hepatitis B virus, and B virus. X ray and skin test (PPD) were performed at entry for all animals to exclude potential carriers of tuberculosis.

A-II MHC class I typing. Rhesus macaque classical MHC class I alleles were genotyped in peripheral blood mononuclear cells (PBMC) samples using sequence-specific primers (SSP) PCR assays for representative Mamu-A and Mamu-B sequences as previously described (Muhl et al., 2002; Loffredo et al., 2007).

A-III Antigenic viral preparations.

III-1. The SIV production was performed on CEM174 cells inoculated with SIVmac239 (gift of P.A. Marx). The culture supernatants were collected at pick viral production.

III-2. AT-2-inactivated SIVmac239: SIVmac239 was inactivated by 250 μM aldrithiol (AT-) (Sigma) for 2 hours and was washed three times by ultracentrifugation. The AT2-inactivated virus was used in a final dose of $10^9$ viral particles for each administration (i.e., vaccination).

III-3. Heat-inactivated SIVmac239: SIVmac239 was inactivated at 56° C. for 30 minutes. The heat-inactivated virus was used in a final dose of $10^9$ viral particles for each administration.

III-4. AT-2-Heat-inactivated SIVmac239: SIVmac239 was inactivated by 250 μM aldrithiol (AT-2) (Sigma) for 2 hours and was washed three times by ultracentrifugation. Then, the virus was subjected to a temperature of 56° C. for 30 minutes. The inactivated virus is used in a final dose of $10^9$ viral particles for each administration.

III-5. The inactivated virus preparations were inoculated to CEM174 cells to verify the 100% inhibition of viral infectivity.

A-IV Assay for Antibody Responses to SIV. Anti-SIV IgG, IgM, and IgA antibodies in plasma were titrated by an immunofluorescence antibody (IFA) assay (Mederle et al., 2003). Briefly, serial twofold dilutions of test plasma were incubated with SIV-infected CEM174 cell-attached slides at 37° C. for 30 minutes. After washing with Hanks, FITC-conjugated goal anti-macaque IgG (Sigma), IgM (ADI, San Antonio, Tex.), or IgA (ADI) were added for additional 30 minutes (at 37° C.). Antibody titers were determined as reciprocal of the highest dilution to reach a positive immunofluorescence staining. The sensitivity of IFA assay was a titer of 20 for IgG and a titer of 5 for IgM and IgA. When a plasma sample was negative for the IFA (below the assay sensitivity), a value of 1 was assigned for facilitating data analysis.

Mucosal secretions were collected by washing of the rectum with PBS using a catheter for gastric instillation as described previously (Tsai et al., 1993). Briefly, trypsin inhibitor (10 μg/ml) and EDTA (5×10-4 M) (Sigma) were added to the samples which were then centrifuged for 10 minutes at 10000×g at 4° C. Supernatants were collected and supplemented with phenylmethylsulfonyl fluoride (10-3 M) and sodium azide (0.01%) (Sigma). Samples were stored at −80° C. until use. Anti-SIV IgA titers in rectum were detected by the above IFA assay.

A-V Flow Cytometry. Flow-cytometry analysis was carried out with FACScalibur (BD Biosciences, San Jose, Calif.) using fluorescence-labeled monoclonal antibodies against the following: CD3-PE-Cy7 (clone SP34-2), CD4-PE (clone MT477), CD8-PerCP (clone RPA-T8), and secondary rabbit anti-mouse-APC (BD Biosciences). The Ki-67-PE (BD Biosciences) and FITC-conjugated anti-P27 monoclonal antibody (Fitzgerald, Concord, Mass.) or biotin-conjugated anti-P27 monoclonal antibody (Fitzgerald) coupled with APC-SAv (BD Biosciences) were used for intracellular staining after permeabilization.

PE-conjugated monoclonal antibodies against TCRγδ (clone B1), Vβ8, and CD antigens (CD7, CD16, CD28, CD62L, CD95, CD122, CD137, CD150, CD183, CD184, CD195, CD196, CD197, CD226, CD272, and CD305) were purchased from BD Biosciences; PE-conjugated monoclonal antibodies against CD antigens (CD11a, CD25, CD27, CD39, CD101, CD129, CD215, CD277, and CD357) were purchased from BioLegend (San Diego, Calif., USA); and PE-conjugated monoclonal antibodies against CD antigens (CD127, CD247, and CD279) were purchased from eBioscience (San Diego, Calif., USA).

A-VI Cell Proliferation. PBMCs were obtained as described previously (Lu et al. 2003). The proliferation of SIV-specific CD4+ or CD8+ T cells was evaluated by carboxy-fluorescein diacetate, succinimidyl ester (CFSE) labeling assay (Molecular Probes, Eugene, Oreg.) according the manufacturer's instruction. PBMC were stained with 3 μM CFSE for 15 minutes at 37° C. After washing, the CFSE-labeled cells were stimulated for 5 days with 10 μg/ml recombinant SIV core protein P27 (ImmunoDiagnostics, Wobun, Mass.), 2 μg/ml SIV gag 15-mer peptides (GLS, Shanghai, China), $10^9$/ml AT-2-inactivated SIV or medium alone. After labeling with anti-CD3 and anti-CD4 or anti-CD8 antibodies, PBMC were fixed in 1% paraformaldehyde for flow cytometry.

A-VII Cell Activation. Fresh PBMCs, depleted (or not) with CD8 or CD25 by magnetic beads were single-round infected with AT-2-treated SIVmac239 for 2 hours at a viral concentration of $10^{10}$/ml. Infected cells were stimulated overnight with staphylococcal enterotoxin B (2.5 μg/ml) and anti-CD3 (2.5 μg/ml)/anti-CD28 (2.5 μg/ml) antibodies. Intracellular staining of SIV P27 and Ki-67 was performed 48 hours after stimulation in order to determine the percentage of activation (Ki-67+) within infected (P27+) CD4+ cells.

A-VIII ELISPOT Assay. The rhesus macaque IFN-γ and IL-10 ELISPOT assays were carried out in uncultured PBMC in the presence or the absence of P27 or AT-2-inactivated SIV using a commercial kit (Cell Sciences, Canton, Mass.). A TGF-b1 ELISPOT kit was purchased from R&D Systems (Minneapolis, Minn.). The data were read with an automated ELISPOT reader (AID, GmbH, Straβberg, Germany). The number of SIV-specific spot forming cells (SFCs) was calculated by subtracting the nonspecific SPCs in the presence of medium alone.

A-IX Antiviral Assay. Autologous CD4+ T cells from each animal purified by magnetic positive-labeling (MicroBeads, Miltenyi Biotec) were acutely infected with SIVmac239 ($10^{-3}$ MOI) in the presence or the absence of magnetically purified CD8+ T cells at a CD4/CD8 ratio of 1:2 and then stimulated with SEB (Sigma) for 16 hours. After washing, the cells were cultured in quadruplicates in a final volume of 200 μl per well of RPMI 1640 medium (Invitrogen, Shanghai, China) containing 100 IU of human rIL2 in 96-well plates for 5 days at 37° C. in the presence of 5% $CO_2$. The cell cultures were replaced once with half of fresh medium at day 3. The culture supernatants collected at day 5 were used for the measurement of viral load by a real-time RT-PCR (see below). Percent suppression (%) was calculated by comparing the geometric mean of viral concentration in the culture supernatants from duplicate wells containing only CD4+ infected cells with the geometric mean of viral concentration in the supernatants from quadruplicate wells containing the mixed CD8+ and CD4+ cells. CD4+ T cells were also co-cultured with allogenic CD8+ T cells in order to determine the correlation between viral suppression and HLA restriction.

A-X Viral Load Measures. SIV RAN in plasma or cell-associated SIV DNA was quantified by a real-time RT-PCR or PCR using primers (sense, SEQ ID No. 1: 5'-GAG-GAAAAGAAATTTGGAGCAGAA-3'; antisense, SEQ ID No. 2: 5'-GCTTGATGGTCTCCCACACAA-3') and probe (SEQ ID No. 3: 5'-FAM-AAAGTTGCACCCCCTAT-GACATTAATCAGATGTTA-TAMRA-3') specifically optimized for SIVmac239 and for SIVmac251.

A-XI SIV-Specific Suppressive T-Cell Assay. Fresh PBMCs, depleted (or not) with either CD8 or CD25 by magnetic bead-conjugated anti-CD8 or anti-CD25 antibodies according to the protocol provided by the manufacturer (Miltenyi Biotec) were infected with SIVmac239 for 2 hours at 0.5 multiplicity of infection (MOI). Infected cells were treated overnight with staphylococcal enterotoxin B (SEB) (2.5 μg/ml) (Sigma) and anti-CD3 (2.5 μg/ml)/anti-CD28 (2.5 μg/ml) antibodies (BD Biosciences). Simultaneous intracellular staining of SIV P27 and Ki-67 were performed 48 hours after in vitro stimulation in order to determine the percentage (%) of T-cell activation (Ki-67+) within infected (P27+) cell populations.

A-XII Viral Challenges.

XII-1. The SIV production was performed on macaques PBMC inoculated with SIVmac239 (gift of P.A. Marx). The culture supernatants were collected at pick viral production.

XII-2. Intrarectal challenge (IRC): Following vaccination, the animals were inoculated (repeatedly) intrarectally with 5000 MID 100 i.e. $5\times10^5$ TCID50 of pathogenic SIVmac239. This infectious dose generally results in a systemic infection of 100% Chinese rhesus macaques with a peak plasma viral load ($10^6$-$10^7$ copies/imp between day 10 and day 14. All SIV-challenged animals were evaluated clinically and biologically every 2-week for 1 month and every 1-month thereafter.

XII-3. Intravenous challenge (IVC): Following vaccination, the animals were inoculated (repeatedly) intravenously with 5 MID 100 i.e. 500 TCID50 (titrated in CEM174 cell line) of pathogenic SIVmac239 (gift of Dr. P.A. Marx from Aaron Diamond AIDS Research Center, New York, USA). This infectious dose generally results in a systemic infection of 100% Chinese rhesus macaques with a peak plasma viral load ($10^6$-$10^7$ copies/ml) between day 10 and day 14. All SIV-challenged animals were evaluated clinically and biologically every 2-week for 1 month and every 1-month thereafter.

A-XIII Statistical Analysis. Impaired data between different groups of animals or paired data before and after immunization were compared by the Mann-Whitney or the Wilcoxon test, respectively.

Part B—Specific Materials & Methods

B-I—Use of BCG as a Tolerogenic Vehicle

B-I-I Preparation of BCG

I-1. Live BCG: Live BCG prepared in Copenhagen at the Statens Serum Institut (strain SSI 1331) was purchased from Laboratories Sanofi-Pasteur Merck, Sharp and Dome (SPMSD) and was used at a final concentration of $5\times10^6$ cfu for intestinal or intravaginal administration or at a final concentration of $5\times10^5$ cfu for each intradermal boost administration.

I-2. Extended freeze drying (EFD) inactivated BCG: The live SSI 133 BCG strain was killed by 5 days extended freeze-drying (EFD) under a vacuum of less than 20 µm Hg and is used at a final dose corresponding to $5\times10^6$ cfu for each intestinal or intravaginal administration or $5\times10^5$ cfu for each intradermal administration.

I-3. Heat inactivated BCG: The live SSI 133 BCG strain was autoclaved for 15 minutes at 115° C. in borate buffer and is used at a final dose corresponding to $5\times10^6$ cfu for each intestinal or intravaginal administration or $5\times10^5$ for each intradermal administration.

B-I-II Pharmaceutical Compositions

The composition was prepared freshly with the use of RPMI 1640 (Invitrogen, Shanghai, China) containing one of the SIV antigens and the tolerogenic vehicle.

B-I-III Animal Immunization

At the time of immunization, animals were anesthetized with tiletamine hydrochloride and zolazepan (0.7 mg/kg) injected intramuscularly.

III-1. Intravaginal immunization (IVI): Female animals were immunized under anesthesia by intravaginal injection for 4 hours of one milliliter of pharmaceutical composition or of one tolerogenic vehicle disclosed previously as a control. A booster immunization with the pharmaceutical composition or with the tolerogenic vehicle was given with the same dose at the same site at 8 weeks. All animals were evaluated clinically and biologically every two weeks after the first immunization.

III-2. Oral (intra-gastric) immunization (IGI): Male or female animals under anesthesia were administered intragastrally with 15 ml of 0.1M sodium bicarbonate 15 minutes before ingestion of pharmaceutical composition or of one tolerogenic vehicle disclosed above as a control. Additional 15 ml of the sodium bicarbonate solution was given immediately after administration. The same tolerogenic vaccination than the initial one was repeated two times at 1-month interval to each animal. All animals were evaluated clinically and biologically every two weeks after the first immunization.

III-3. Intradermal boost immunization (IDI): Female intravaginally immunized animals (see above IVI section) were given at 90 days after the first immunization under anesthesia an intradermal booster with 0.1 ml of pharmaceutical composition containing $10^9$ copies of AT-2-inactivated SIV and $5\times10^5$ cfu of live BCG. All animals were evaluated clinically and biologically every two weeks after the first immunization.

B-I-IV Antiviral Assay. The threshold corresponding to sterile immunity after intrarectal challenge is at least 20.

B-II—Use of *Lactobacillus plantarum* as a Tolerogenic Vehicle

B-II-I Bacterial Preparation (Tolerogenic Vehicle Preparation). *Lactobacillus plantarum* (LP) (ATCC8014) was cultured at 37° C. in MRS medium with a rotation rate of 200 rpm. To obtain LP at the logarithmic (midlog) phase of bacterial culture, bacteria were cultured until reaching an optical density of 1.0 at 600 nm with a final LP concentration of around $10^{10}$ cfu/ml (obtained in about 3.5 hours).

B-II-II Animal Immunization by Oral (Intra-Gastric) Delivery. Animals were fasted overnight (without breakfast). At the time of oral administration, animals were anesthetized with tiletamine hydrochloride and zolazepan (0.7 mg/kg) injected intramuscularly.

Immunisation No. 1: Eight animals were administered intragastrically 30 ml of a made of a viral-bacterial preparation containing $4\times10^7$ copies/ml of DI-SIV and $3\times10^9$ cfu/ml of living LP in maltodextrin (20%) solution. After this first immunization, monkeys were receiving intragastrically 25 ml of the same viral-bacterial preparation (i.e., pharmaceutical composition) each 30 minutes for 3 hours. This oral delivery protocol was performed 5 times over 5 consecutive working days. As controls 4 animals were administered living LP alone and other 3 received only twice inactivated SIV in parallel.

Immunisation No. 2: Twelve animals (iSIV/LP#9-20) were intragastrically administered 30 ml of a preparation of $4\times10^7$ copies/ml of iSIV (AT-2/heat-inactivated SIVmac239) and $3\times10^9$ cfu/ml of living LP in maltodextrin (20%) solution. Then, animals were receiving 25 ml of the same preparation every 30 minutes for 3 hours (6 times) on 5 consecutive days. Six animals (LP#5-10) were intragastrically administered 30 ml of $3\times10^9$ cfu/ml of living LP in maltodextrin (20%) solution. Then, animals were receiving 25 ml of the same preparation every 30 minutes for 3 hours (6 times) on 5 consecutive days. Finally, another 6 animals (iSIV#5-10) were intragastrically administered 30 ml of a preparation of $4\times10^7$ copies/ml of iSIV alone. Then, animals were receiving 25 ml of the same preparation every 30 minutes for 3 hours (6 times) on 5 consecutive days.

B-II-III Depletion of CD8$^+$ T Cells In Vivo. Macaques were first anesthetized and then given an intravenous injection of a chimeric anti-CD8 monoclonal antibody (cMT-807, Centocor Research & Development, Inc., Malvern, Pa., USA) at 5 mg/kg on days 0, 4, and 7 as described earlier (Schmitz et al., 1999). Peripheral blood samples (5 ml) were taken from each animal at day 0 and at various time points after antibody injection.

B-II-IV Antiviral Assay. The threshold corresponding to sterile immunity after intrarectal challenge is at least 100.

B-II-V CD8+ T Cell SIV Suppression Assay. Autologous CD4+ T cells from each animal purified by magnetic positive-labeling (MicroBeads, Miltenyi Biotec) were acutely infected with SIVmac239 ($10^{-3}$ multiplicity of infection) in the presence or the absence of magnetically purified CD8+ T cells at a CD4/CD8 ratio of 1:3 and then stimulated with SEB and anti-CD3/anti-CD28 antibodies for 16 hours. After washing, the cells were cultured in quadruplicates in 96-well plates. Cultures were maintained in a final volume of 200 µl per well of RPMI 1640 medium containing 100 IU of human rIL2 (Roche Diagnostics GmbH, Mannheim, Germany) for 5 days. Culture supernatants collected at day 5 were used for the measurement of viral load by a real-time RT-PCR (see below). Fold suppression was calculated as follows: the geometric means of viral concentration in the culture supernatants from the infected CD4+ target cells only/the geometric means of viral concentration in the supernatants from the mixed CD8+ and CD4+ T cells).

In some experiments, CD8+ and CD4+ T cells were cultured without cell-to-cell contact by using a Multiwell Insert System (BD Biosciences) (CD8 in the insert well and CD4 in the bottom well); CD4+ T cells were cocultured with allogenic CD8+ T cells in order to determine the correlation between viral suppression and MHC restriction; and CD8+ and CD4+ T cells were also co-cultured in the presence of anti-MHC-ABC (BioLegend) or anti-MHC-E (Cell Science) antibodies to define the modes of MHC restriction. To define the subsets of CD8+ T cells associated with antiviral activity, CD8+ T cells were purified from PBMCs immediately after their depletion with PE-conjugate anti-TCRγδ, anti-Vβ8, or other anti-CD antigen antibodies using anti-PE microbeads through a LD column (Miltenyi Biotec).

B-II-VI SIV-Specific CD8+ T Cell's Cytotoxicity Assay. Both purified CD8+ T cells (effector cells) and purified CD4+ T cells pulsed with $10^{10}$ AT-2-treated SIVmac239 (target cells) were labeled with 40 nM 3,3'dihexyloxacarbocyanine ($DiOC_6$) (Marchetti et al., 1996) (Molecular Probes) for 10 min at 37° C. Target cells were labeled with PerCP-Cy5-conjugated anti-CD4 (BD Bioscience) for 20 min on ice. After washing 3 times, effector cells were mixed with target cells in a U-bottomed 96-well plate at different E/T ratios (3:1, 1:1, 0.3:1) in triplicate. K562 cells (target) with APC-conjugated anti-CD32 (BD Bioscience) and purified CD56+ (NK) cells (effector) from 4 healthy donors were included as an assay control. After 4 hrs incubation at 37° C. in the presence of SEB and anti-CD3/anti-CD28, cells were harvested and analyzed by flow cytometry. Percent cytotoxicity was calculated as follows: 100×(% of total apoptotic target cells–% of spontaneous apoptotic target cells)/(100–% of spontaneous apoptotic target cells).

B-II-VII Viral Challenges.

First Study: Four months after the oral administration of the vaccine or the controls in the first batch of experiment (immunization No. 1), the 8 immunized animals and their 7 controls were inoculated intra-rectally with 2500 $MID_{100}$ (100.000 $TCID_{50}$) of pathogenic SIVmac239. Two months later, 4 vaccinated and already protected monkeys were rechallenged by intrarectal route (100.000 $TCID_{50}$) while the 4 other protected monkeys were intravenously rechallenged with 5 $MID_{100}$ (200 $TCID_{50}$) of SIVmac239. As controls, 2 monkeys received an intrarectal challenge and other 2 an intravenous challenge. These infectious doses generally result in a systemic infection of 100% Chinese rhesus macaques with a peak plasma viral load ($10^7$-$10^9$ vp/ml) between day 10 and day 14.

Second Study (Immunization No. 2): On day 420 post-immunization in the second set of study, 16 animals (8 monkeys immunized with iSIV and LP) and 8 controls (4 iSIV and 4 LP) were intrarectally challenged with 100,000 $TCID_{50}$ of SIVmac239.

Part C—Results

C-I BCG is a Tolerogenic Vehicle

C-I-I Protection Against the Intravenous SIVmac239 Challenge Following Intravaginal Administration:

Six animals (Compositions_1, 2, 3, 4, 5, and 6) were administered intravaginally one milliliter of a tolerogenic composition comprising AT2-inactivated virus as an antigen and live BCG. A booster administration was given with the same tolerogenic composition at the same site at 8 weeks.

Simultaneously, 5 other animals (controls_1, 2, 3, 4, and 5) were given intravaginally one milliliter of a composition comprising only live BCG. A booster administration was also given with the same composition at the same site at 8 weeks.

Four months after the initial administration, all 11 animals (Compositions_1-6 and controls_1-5) were challenged by an intravenous viral inoculation.

The viral loads were determined regularly in the plasma of the treated animals.

FIG. 1 shows the virus loads (plasma SIV RNA copies/ml) as a function of time (days) in animals which have received the composition (Compositions_1-6) and in control animals (controls_1-5) following a single intravenous viral challenge.

The results show that, after intravenous viral challenge, the 5 control animals (Controls_1-5) showed a typical primary infection with a peak plasma viral load ($10^6$-$10^7$ copies/ml) between days 10-14 post-challenge as expected. The plasma viral load of this group of control animals remained still high (>$10^5$ vp/ml) over the 60 days post viral-challenge and thereafter.

In contrast, 4/6 animals which had received intravaginally the tolerogenic composition made of an AT-2-inactivated SIVmac239 plus BCG showed a very low plasma viral load peak (<1000 vp/ml; between days 10-14), which became undetectable (<10 vp/ml) rapidly (one month after viral challenge). The 2 animals with a high plasma viral load peak (>$10^6$ copies/ml) had a lower set-point viral load level (<1000 copies/ml) than the control group (>$10^5$ copies/ml) at day 60.

C-I-II—Protection Against the Intrarectal SIVmac239 Challenge Following Intravaginal Administration of the Composition:

Seven animals (Compositions_7, 8, 9, 10, 11, 12, and 13) were administered intravaginally one milliliter of a tolerogenic composition comprising AT2-inactivated virus as an antigen and live BCG as a tolerogenic vehicle. A booster administration was given with the same composition at the same site at 8 weeks.

Simultaneously, five other animals (controls_6, 7, 8, 9, and 10) were given intravaginally one milliliter of a composition comprising only live BCG. A booster administration was also given with the same composition at the same site at 8 weeks.

Four months after the initial administration, all 12 animals (Compositions_7-13 and controls_6-10) were challenged with SIVmac239 through an intrarectal viral inoculation.

The viral loads were determined regularly in the plasma of the treated and control animals.

Figure 2:
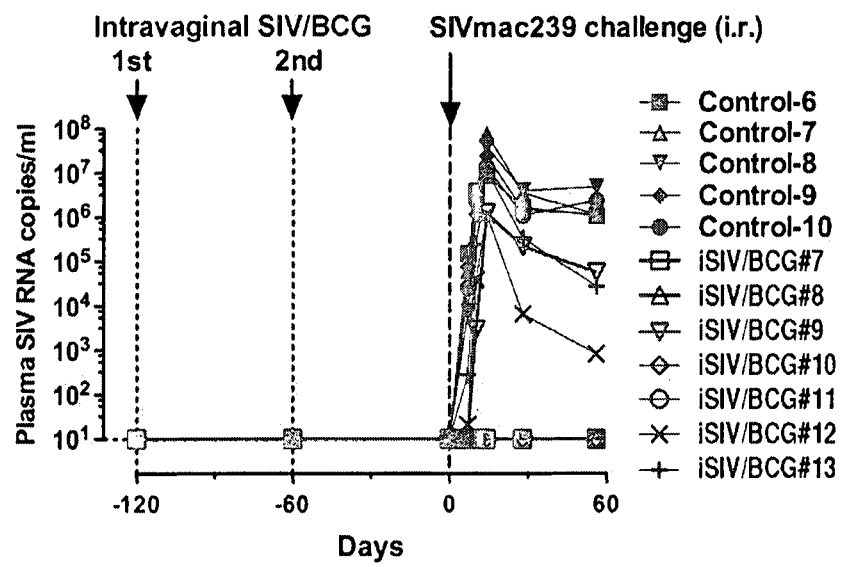
FIG. 2: Intrarectal (i.r.) SIVmac239 challenge of rhesus macaques pretreated with an intravaginal iSIV/BCG.

FIG. 2 shows the virus loads (plasma SIV RNA copies/ml) as a function of time (days) in animals which received the composition (Compositions_7-13) and in control animals (controls_6-10) following intrarectal viral challenges.

The results show that, following intrarectal viral challenges, the 5 animals which received the intravaginal administration of live BCG alone (Controls_6-10) showed a typical primary infection with a peak plasma viral load ($10^6$-$10^7$ vp/ml) between days 10-14 post-challenge as expected. The plasma set-point viral load of this group of control animals remained still high (>$10^5$ copies/ml) over the 60 days post viral-challenge.

In contrast, 4/7 animals which received intravaginally AT-2-inactivated SIVmac239 plus live BCG showed surprisingly undetectable viral load level (<10 copies/ml) over a period of 60 days post-challenge. The 3 other animals showed a typical primary infection with a peak plasma viral load between days 10-14 post-challenge. However, their set-point viral load ($10^3$-$10^5$ copies/ml) was significantly lower than the control animals' level (>105).

C-I-III—Protection Against Repeatedly Intravenous or Intrarectal SIVmac239 Challenges Following Intravaginal Administration of the Pharmaceutical Composition:

Two and eight months later, the 3 animals with an undetectable viral load following intravenous challenge (Compositions_1, _2, and _3) were subjected to a second and a third intravenous challenge with the same dose of viral inocula.

After the second and third intravenous viral challenges of this group of monkeys, a similar low peak plasma viral load was observed at day 10. However, by 30 days after viral challenge, viral loads became again undetectable (FIG. 3).

Sixteen and twenty three months after the initial administration of the composition, the 3 animals which already had a total of 3 intravenous challenges (Compositions_1, _2, and _3) were further challenged by intrarectal inoculation.

Figure 3:
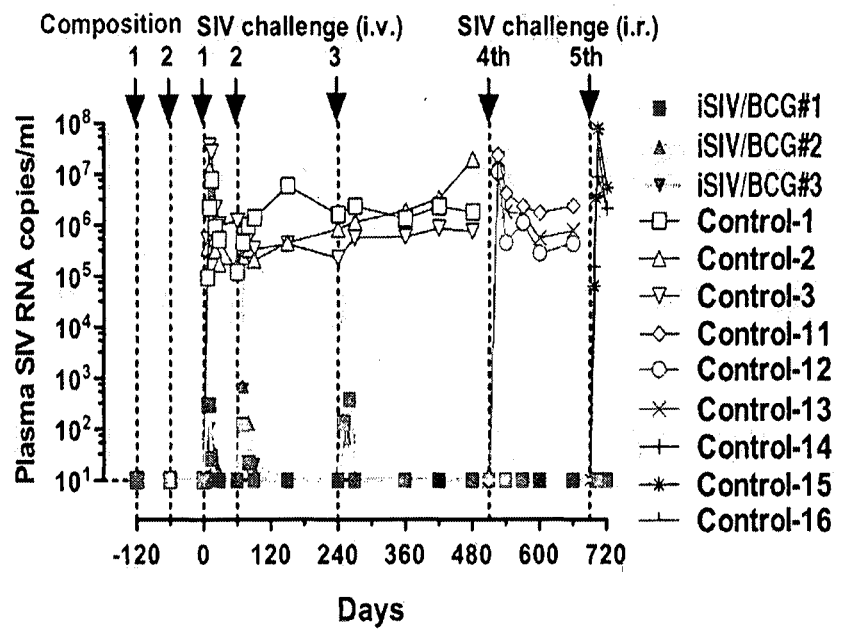
FIG. 3: Repeated SIVmac239 challenges (3 times by i.v. and 2 times by i.r.) of rhesus macaques pretreated with an intravaginal iSIV/BCG.

As expected, these 3 animals (which initially received intravaginally AT-2-inactivated SIVmac239 plus BCG) showed again no detectable (<10 copies/ml) plasma viral load peak after 2 successive intrarectal viral challenges (FIG. 3).

These results have established that efficiency on inhibiting viral replication is stable since this inhibition is still observed more than 20 months after the initial administration of the composition C-I-IV—Protection Against the Intravenous or Intrarectal SIVmac239 Challenge Following Intravaginal Administration of the Pharmaceutical Composition Plus an Intradermal Booster:

As expected, after following intravenous (controls 17 and 18, FIG. 4) or intrarectal (controls 19 and 20, FIG. 5) viral challenges, the 4 animals which had received intravaginal administration of live BCG alone showed a typical primary infection with a peak plasma viral load ($10^6$-$10^7$ vp/ml) between days 10-14 post-challenge as expected. The plasma set-point viral load of this group of control animals remained still high (>$10^5$ copies/ml) by 60 days post viral challenge.

Figure 4:
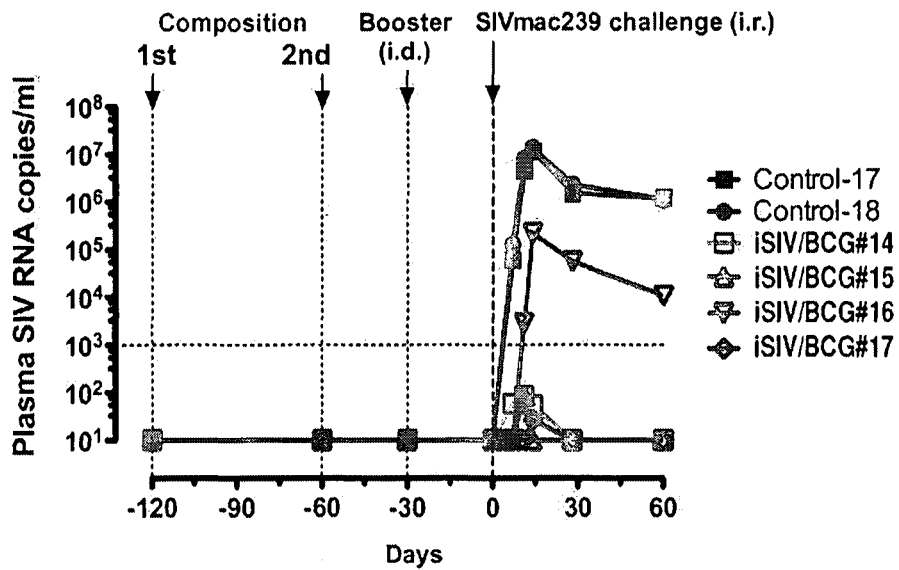
FIG. 4: Intravenous SIVmac239 challenge of rhesus macaques pretreated with an intravaginal iSIV/BCG plus an intradermal booster.

In contrast, the 3/4 (75%) animals (Compositions 14, 15, and 17) which received intravaginally the composition made of AT-2-inactivated SIVmac239 and live BCG plus an intradermal booster with the same composition showed undetectable plasma viral load (<10 copies/ml) over a period of 60 days post-intravenous challenge (see FIG. 4). The remaining one animal (composition 16) showed a primary infection with a peak plasma viral load (>$10^5$ copies/ml) between days 10-14 post-challenge (see FIG. 4). However, its set-point viral load reached relatively low level ($10^4$ copies/ml) at day 60.

Figure 5:
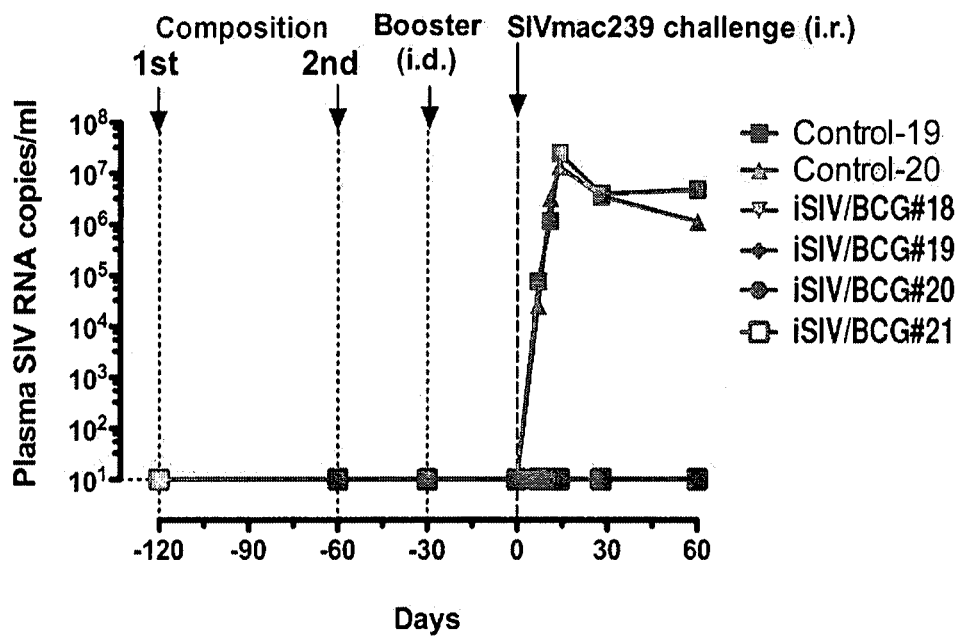
FIG. 5: Intrarectal SIVmac239 challenge of rhesus macaques pretreated with an intravaginal iSIV/BCG plus an intradermal booster.

Moreover, the 4/4 (100%) animals (compositions 18-21) which received intravaginally the composition made of AT-2-inactivated SIVmac239 plus live BCG plus an intradermal booster of the same composition showed undetectable plasma viral load (<10 copies/ml) over a period of 60 days post-intrarectal challenge (see FIG. 5).

C-I-V—Protection Against the Intrarectal SIVmac239 Challenge Following Oral Administration of the Pharmaceutical Composition:

Four animals (Compositions_22, _23, _24, and _25) were administered intragastrically one milliliter of a composition comprising AT2-inactivated virus and live BCG.

Simultaneously, four other animals (controls 21-24) were intragastrically given one milliliter of live BCG alone.

The same administration given initially to each animal was repeated three times at day 15, 30 and 60 following the first administration step.

Figure 6:
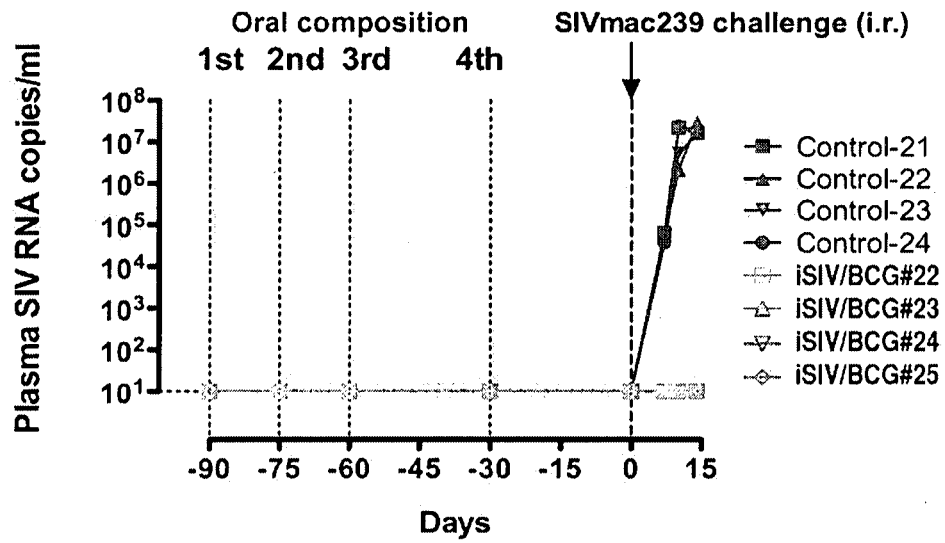
FIG. 6: Intrarectal SIVmac239 challenge of rhesus macaques pretreated with an oral iSIV/BCG.

The results show that after intrarectal viral challenge (performed at day 90), the 4 animals which received live BCG alone (controls 21-24) showed a typical primary infection with a peak plasma viral load ($10^6$-$10^7$ copies/ml) between days 10-14 post-challenge whereas the 4 animals (Compositions_22-25) which received the AT-2-inactivated SIV plus live BCG composition showed surprisingly an undetectable plasma viral load (<10 copies/ml; between days 10-14) (FIG. 6).

C-I-VI—Immune Correlates and Protection Against SIVmac239 Challenge Following the Administration of the Composition Made of AT2-Inactivated Virus Plus Live BCG:

No systemic antibody directed against SIV was detected in the blood of the treated animals. However, some specific systemic humoral response has been detected when intradermal boost composition administration has been used. Consequently, the observed protection against SIV infection for the treated animals does not result from a systemic humoral response.

Moreover, no conventional SIV-specific gamma interferon-producing cytotoxic T lymphocytes were detectable by ELIspot (data not shown). For the purpose of evaluating whether a SIV-specific non-conventional cellular response existed, blood samples were taken for each treated or control animal, and CD4+ and CD8+ cells were purified from each sample according to conventional methods. The previously obtained CD4+ cells were cultured and then infected with SIV mac239 according to conventional methods. The SIV-infected CD4+ cells were then cultured in the presence or in the absence of the previously obtained autologous CD8+ cells for 5 days. The supernatant SIV concentration was assayed by a quantitative real-PCR.

Figure 7:
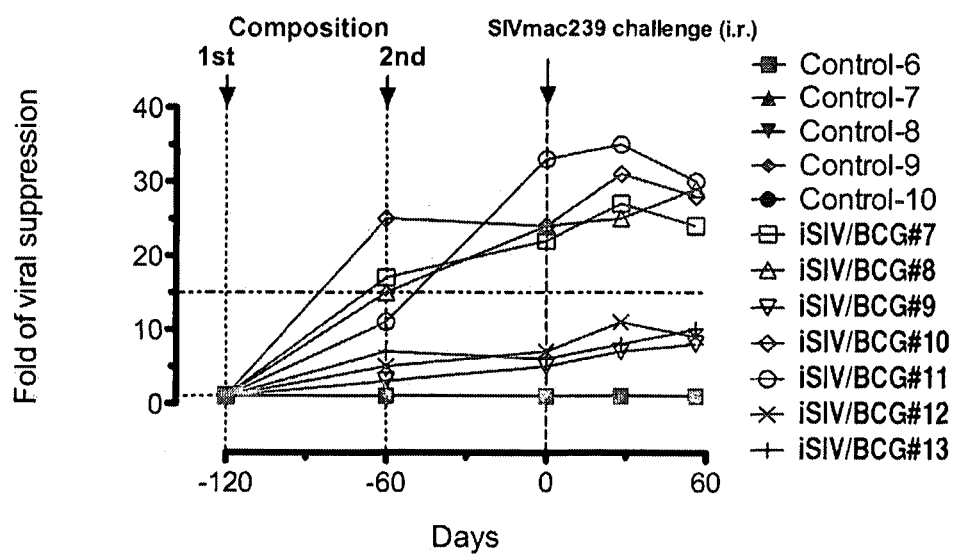
FIG. 7: In vitro antiviral activity of CD8+ T cells obtained from rhesus macaques pretreated with an intravaginal iSIV/BCG.

FIG. 7 shows the fold of suppression of viral replication in SIV-infected CD4+ obtained in the presence or in the absence of autologous CD8+ cells obtained in the course of the experiments presented in FIG. 2. The tested CD8 were obtained from animals which received, by the intravaginal route, the composition of AT2-inactivated virus plus BCG (Compositions_7-13) or from control animals (controls 6-10).

The results show that the CD8 T cells from animals protected against virus infection (composition_7, composition _8, composition _10, and composition _11) provide a level of viral suppression in SIV-infected CD4 cells greater than 20 fold, whereas the CD8 T cells from animals non-protected against virus infection (composition_9, composition_12, and composition_13) provide a level of viral suppression inferior or equal to 10 fold (FIG. 7). Moreover, a more than 20 fold viral suppression has been also observed in the 4 animals protected against intravenous viral challenges presented in FIG. 1 (data not shown).

Figure 8:
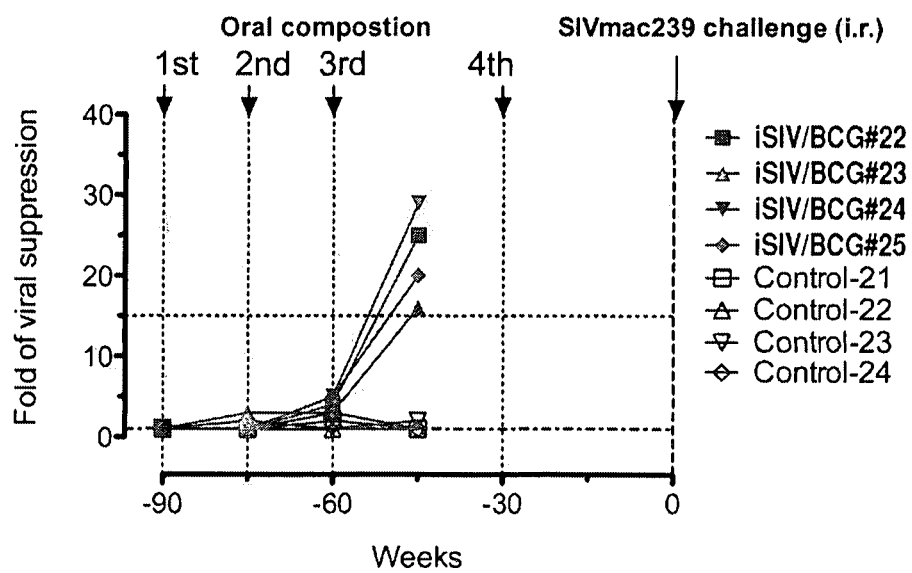
FIG. 8: In vitro antiviral activity of CD8+ T cells obtained from the 4 rhesus macaques pretreated with an oral iSIV/BCG.

FIG. 8 shows the levels of viral suppression in SIV-infected CD4+ obtained in the presence or in the absence of autologous CD8+ cells obtained in the course of the experiments presented in FIG. 6. The tested CD8 were obtained from the 4 animals which received the composition (compositions_22-25) by oral administration of AT2-inactivated virus plus BCG or from the 4 control animals (controls 21-24).

Figure 9:
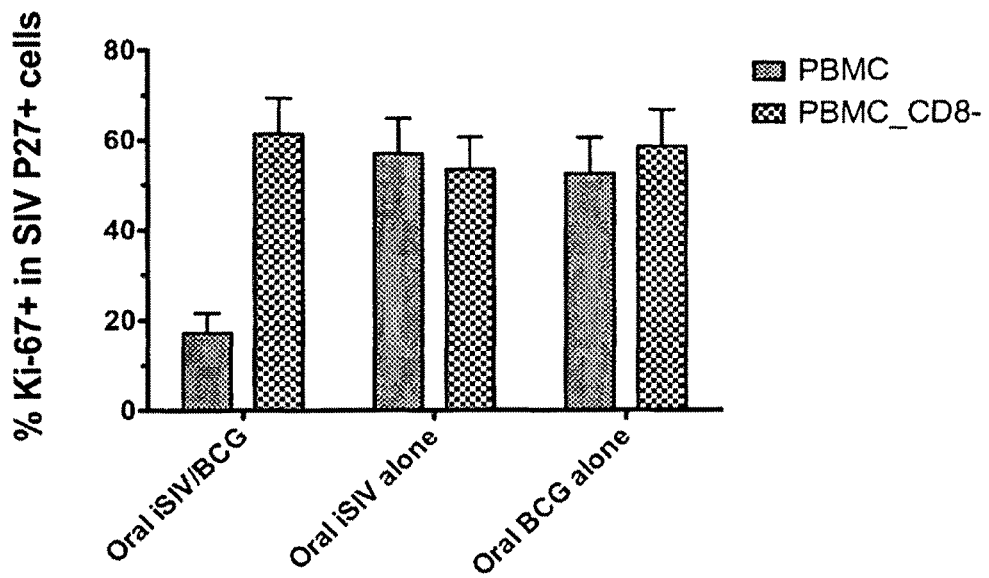
FIG. 9: SIV-specific suppression of CD4+ T-cell activation by autologous CD8+ T cells obtained from the 4 rhesus macaques pretreated with an oral iSIV/BCG.

FIG. 9 shows the levels of T-cell activation (Ki-67+) in SIV (P27+)-infected CD4 cell population obtained in the presence or in the absence of autologous CD8+ cells obtained in the course of the experiments presented in FIG. 6. The tested CD8 were obtained from the 4 animals which received the composition (compositions_22-25) by oral administration of AT2-inactivated virus plus BCG or from the 4 control animals (controls 21-24). A SIV-specific suppression of CD4+ T-cell activation by autologous CD8+ T cells was observed in the 4 animals which received the composition.

The results confirm that the prevention of systemic or mucosal SIV infection obtained by intravaginal or oral administration of AT2-inactivated plus BCG induced a state of immunotolerance characterized by a non-cytotoxic CD8+ T-cell response associated with an SIV-infected CD4 cell anergy. In view of these results, BCG can thus be identified as a tolerogenic adjuvant.

Taken together, these findings have demonstrated that a steady state of immunotolerance to SIV antigens is for the first time achieved by intravaginal or oral (or intragastric) administration of a composition made of inactivated SIV virus plus live BCG. At the same time, it was shown for the first time that an intravaginal or oral administration of a pharmaceutical composition comprising AT2-inactivated SIV virus plus live BCG according to the invention is effective (>50%) to prevent chronic viral infection following intrarectal or intravenous challenge.

C-II—Use of *Lactobacillus plantarum* as a Tolerogenic Vehicle

C-II-I—Induction of SIV-Specific Immunotolerance by Oral Co-Administration of Double Inactivated SIV and *Lactobacillus plantarum* (iSIV/LP)

Figure 10A:
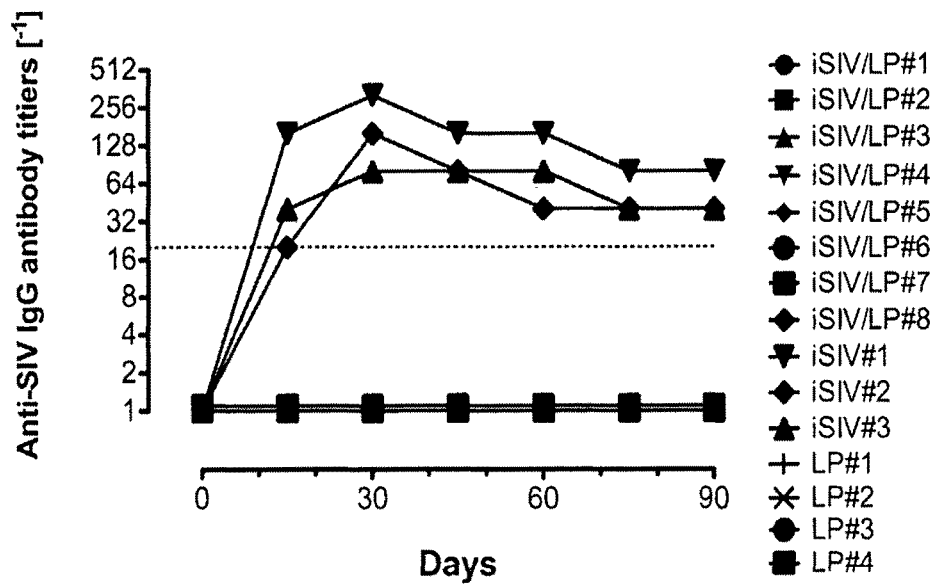
FIG. 10a: Anti-SIV IgG antibody titers in plasma samples taken from the rhesus macaques pretreated with iSIV/LP, iSIV or LP.

On the one hand, SIV-specific antibodies (IgG, IgM, and IgA) were not detected in animals treated with oral iSIV/LP (FIG. 10a). On the other hand, no significant SIV P27-specific peripheral blood CD4+ T cell proliferation was observed in iSIV/LP-treated animals while iSIV-treated animals did show significant P27-specific peripheral blood CD4+ T cell proliferation.

C-II-II—Anti-Activation and Antiviral Activities of Non-Cytotoxic CD8+ Cells

Figure 10B:
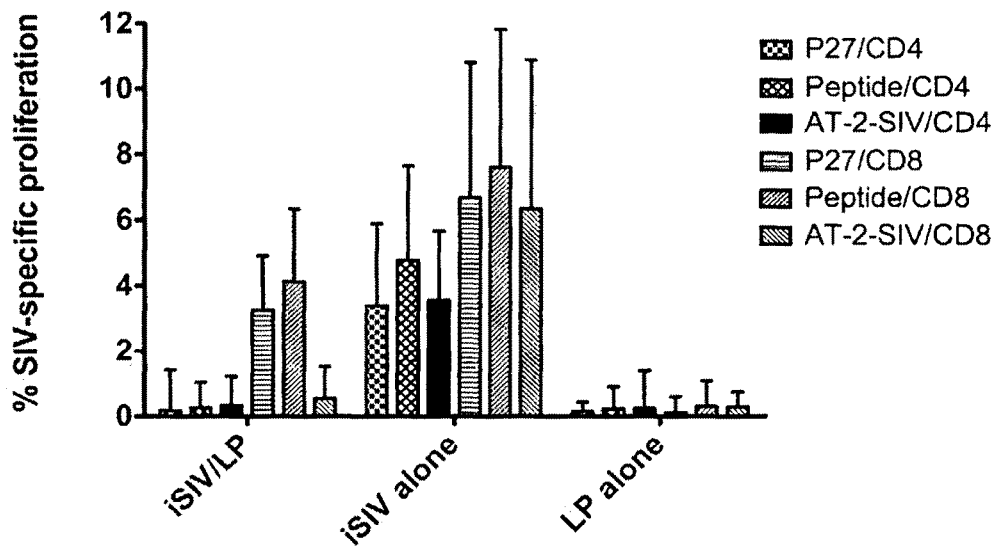
FIG. 10b: SIV-specific T-cell proliferation in PBMC samples taken from the rhesus macaques pretreated with iSIV/LP, iSIV or LP.
Figure 10C:
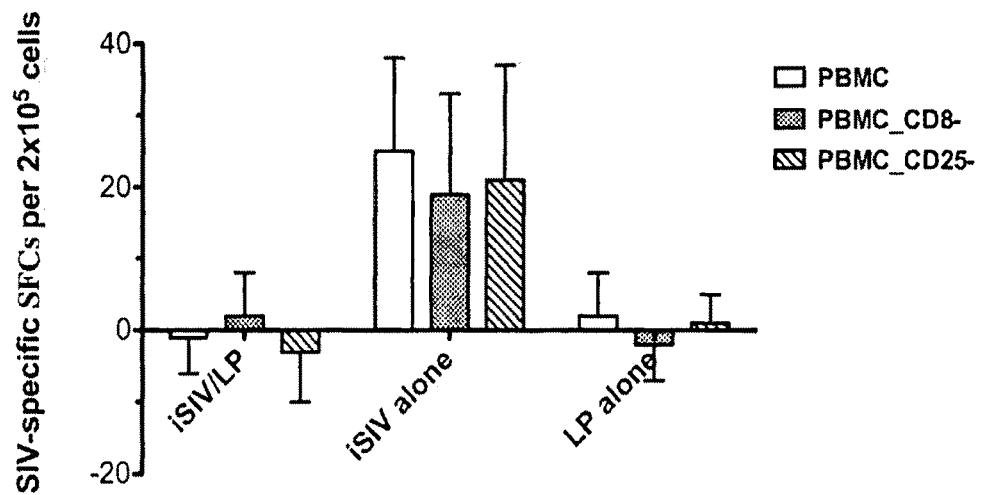
FIG. 10c: SIV-specific IFN-gamma-secreting T cells upon in vitro stimulation in the presence or the absence of CD8 or CD25 T cells.
Figure 10D:
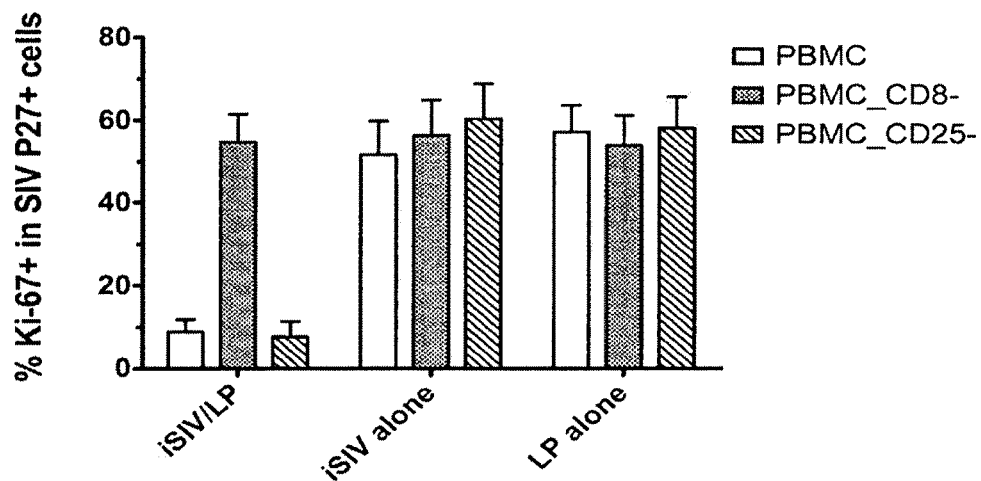
FIG. 10d: SIV-specific suppression of CD4+ T-cell activation by autologous CD8+ T cells obtained from the 8 rhesus macaques pretreated with an oral iSIV/LP as compared to animals pretreated with an oral LP (n=4) or iSIV (n=3).

SIV P27-specific peripheral blood CD8+ T cell proliferation was observed both in iSIV/LP-treated and iSIV-treated animals (FIG. 10b). However, no interferon-gamma secreting T cells (upon to in vitro stimulation) were detected in iSIV/LP-treated animals and the depletion of either CD8+ or CD25+ cells did not alter the unresponsiveness of P27-specific effector T cells (FIG. 10c). Moreover, a strong suppression of activation (Ki-67+) of infected (P27+) CD4+ T cells by non-cytotoxic CD8+ T cells was also observed in acutely in vitro infected PBMCs taken from iSIV/LP-treated animals and the depletion of CD25+ cells did not alter the potent suppression operated by CD25-CD8+ T cells on the activation of infected CD4+ T cells (FIG. 10d).

Figure 10E:
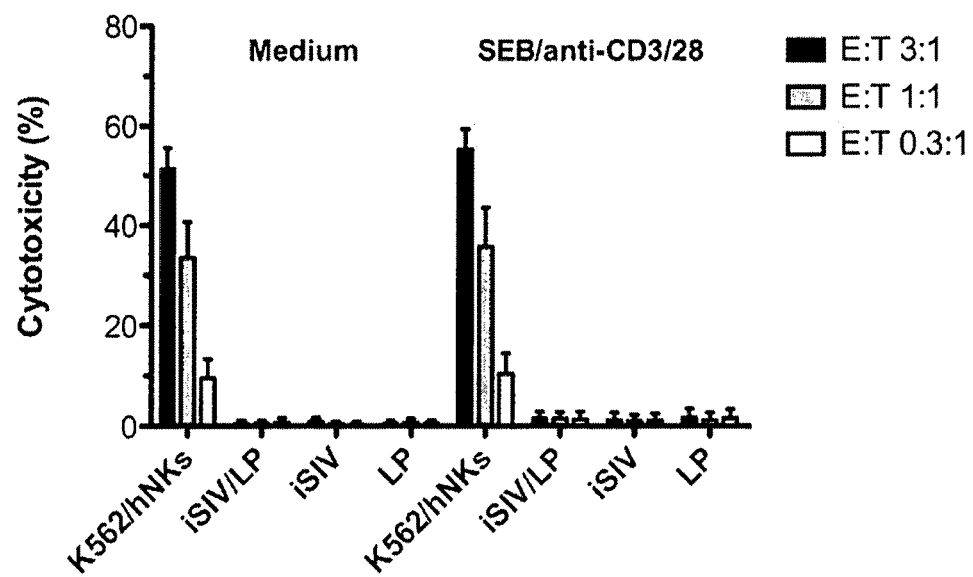
FIG. 10e: SIV-specific CD8+ T cells after 60 days following intragastric administration of an iSIV/LP preparation: cytotoxicity of AT-2 SIV-pulsed CD4+ T cells in the presence of CD8+ T cells or of K562 in the presence of human nature killer cells (hNK) (controls) with or without SEB and anti-CD3/CD28 stimulation.

Of note the fact that no cell lysis was detected by a high-sensitive cytotoxicity assay (Marchetti et al., 1996) after co-incubating CD8+ T cells and CD4+ T cells pulsed with non-replicative SIVmac239 in the presence or the absence of SEB and anti-CD3/anti-CD28 antibodies (FIG. 10e).

Figure 11A:
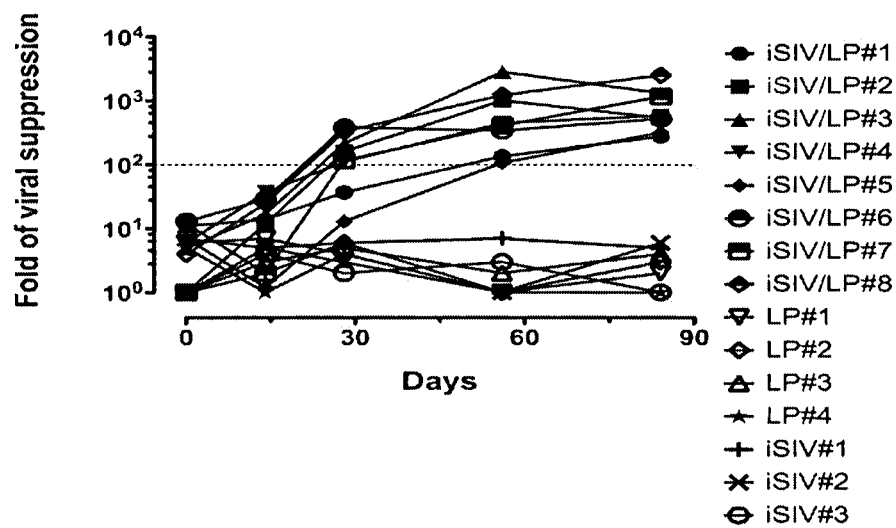
FIG. 11a: In vitro antiviral activity (in CD4 cells) of autologous CD8+ T cells obtained from the 8 rhesus macaques pretreated with an oral iSIV/LP as compared to animals pretreated with an oral LP (n=4) or iSIV (n=3).
Figure 11B:
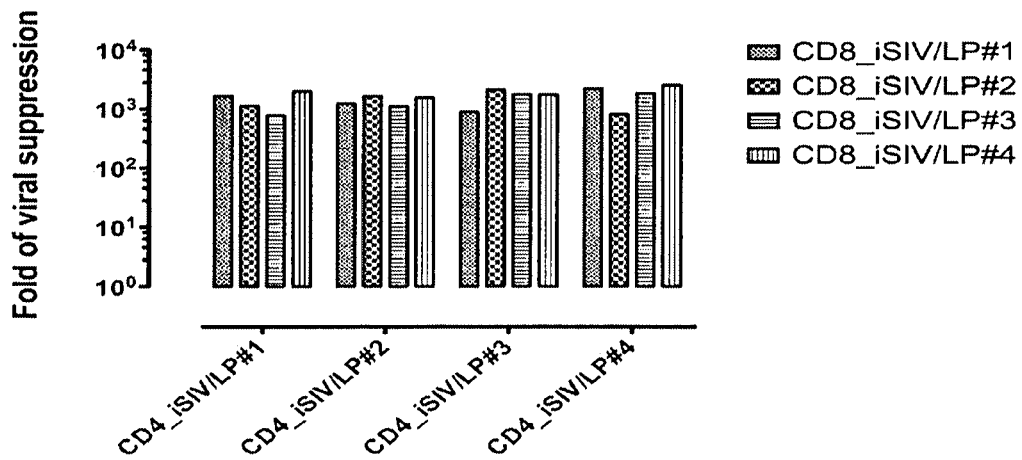
FIG. 11b: In vitro antiviral activity (in CD4 cells) of heterologous or allogenic CD8+ T cells obtained from 4 out of the 8 rhesus macaques 80 days after the treatment of an oral iSIV/LP.

Finally, the peripheral blood CD8+ T cells taken from animals treated since 2 months by iSIV/LP showed a strong inhibiting activity against viral replication in acutely in vitro infected autologous CD4+ T cells (FIG. 11a). Furthermore, such a strong antiviral activity of CD8+ T cells was also observed equally in acutely in vitro infected heterologous CD4+ T cells (FIG. 11b), suggesting that a non classical HLA1 restricted mechanism is involved in the suppressive/inhibiting activity of CD8+ T cells.

Figure 11C:
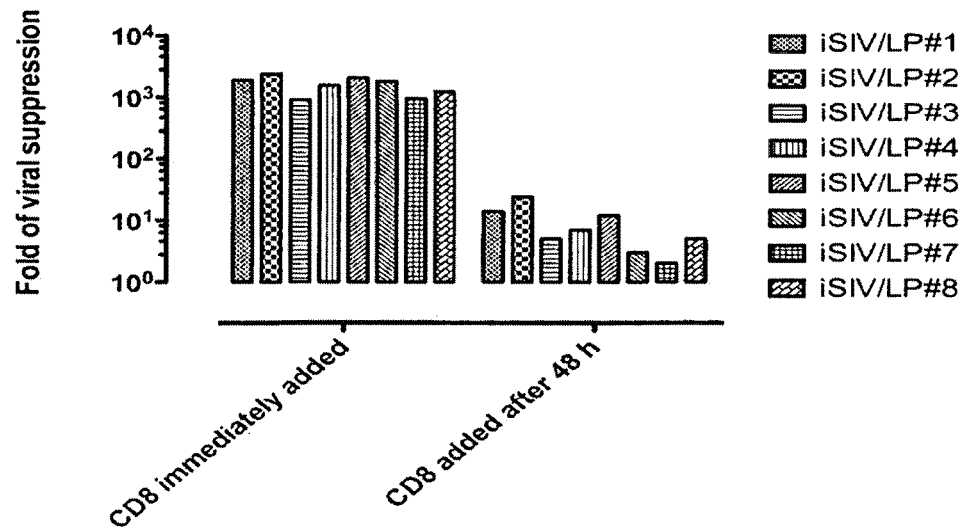
FIG. 11c-g: Anti-SIV activity of CD8+ T cells after 60 days following oral immunization in a delayed (c), insert (d), allogenic (e) culture system, in the presence of anti-MHC-Ia/ABC or anti-MHC-Ib/E antibodies (f), and in the CD8+ T cells depleted of TCR$\gamma\delta^+$ or V$\beta 8^+$ subset (g).
Figure 11D:
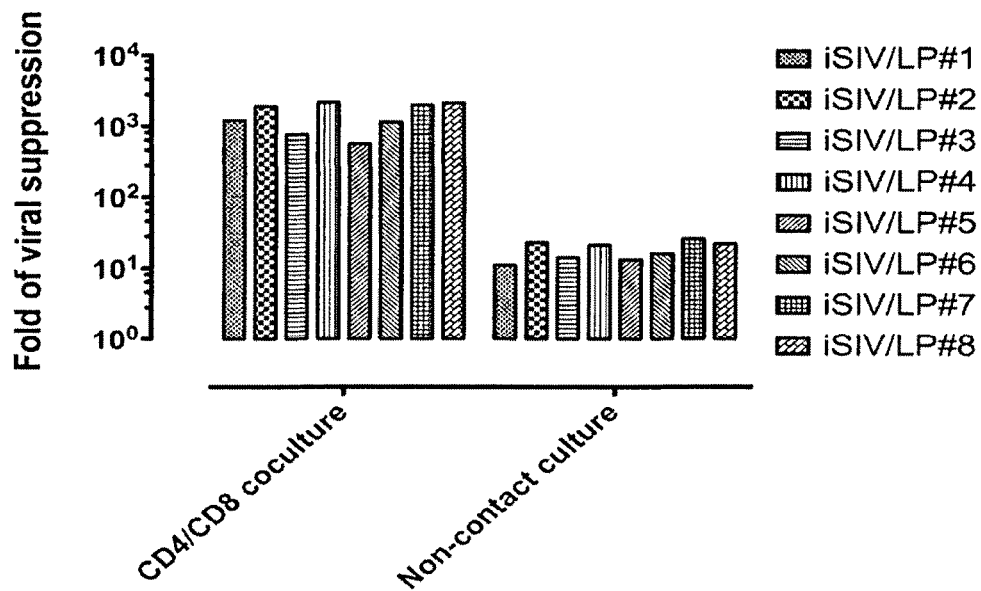
Figure 11E:
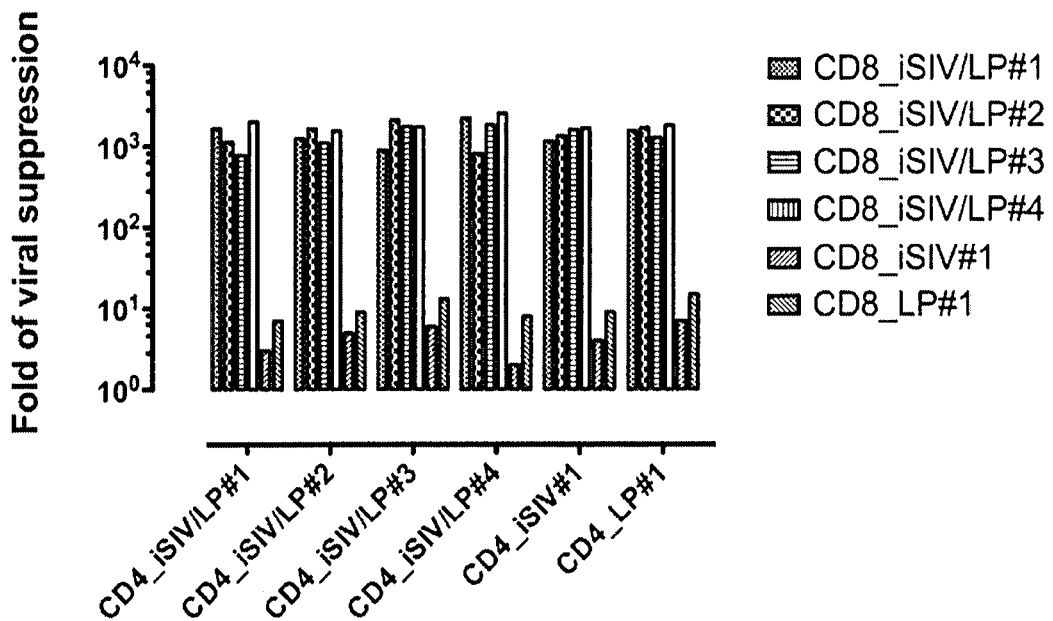
Figure 11F:
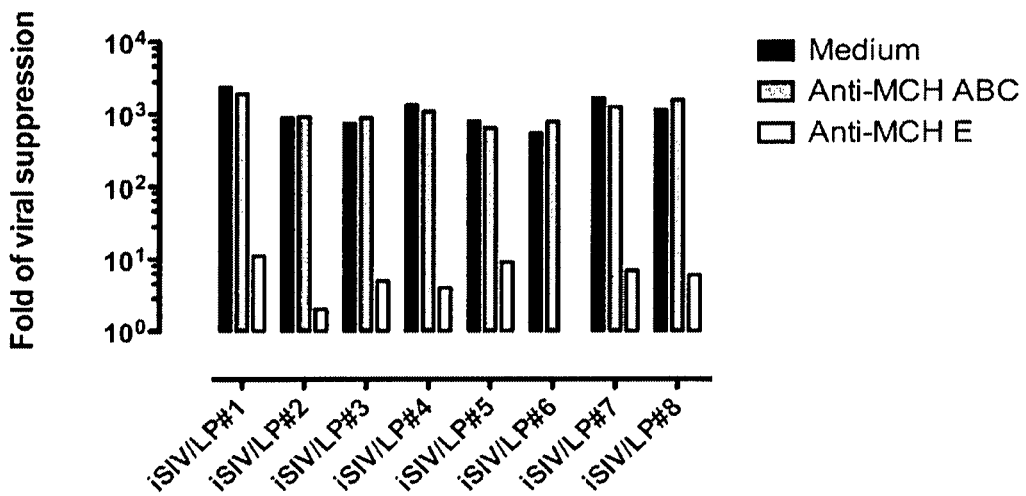

Purified peripheral blood CD8+ T cells taken from macaques immunized with LP/iSIV≥2 months earlier had a strong antiviral activity on autologous acutely SIVmac239-infected CD4+ T cells stimulated overnight with SEB and anti-CD3/anti-CD28 antibodies and then co-cultured for 5 days. Once SIV-specific CD4+ T cells activation is established (48 hours post-stimulation), adding CD8+ T cells can no longer inhibit viral replication (FIG. 11c). This observation argues against the potential lysis of target (productively infected) CD4+ T cells by CD8+ T cells in prolonged culture, as suggested by a previous study in human autoimmune type 1 diabetes (Jiang et al., 2010). This CD8+ T cell-mediated antiviral activity needed cell-to-cell contact (FIG. 11d) and also was classical MHC1a-unrestricted as shown by the strong inhibition of viral replication operated by CD8+ T cells on acutely infected CD4+ T cells from other immunized animals or from control animals (FIG. 11e). Finally, the CD8-mediated antiviral activity was blocked by an anti-MHC-Ib/E antibody but not by the anti-MHC-la/ABC antibody, indicating a non-classical MHC-Ib/E-restricted CD8+ T cell activity (FIG. 11f).

Figure 11G:
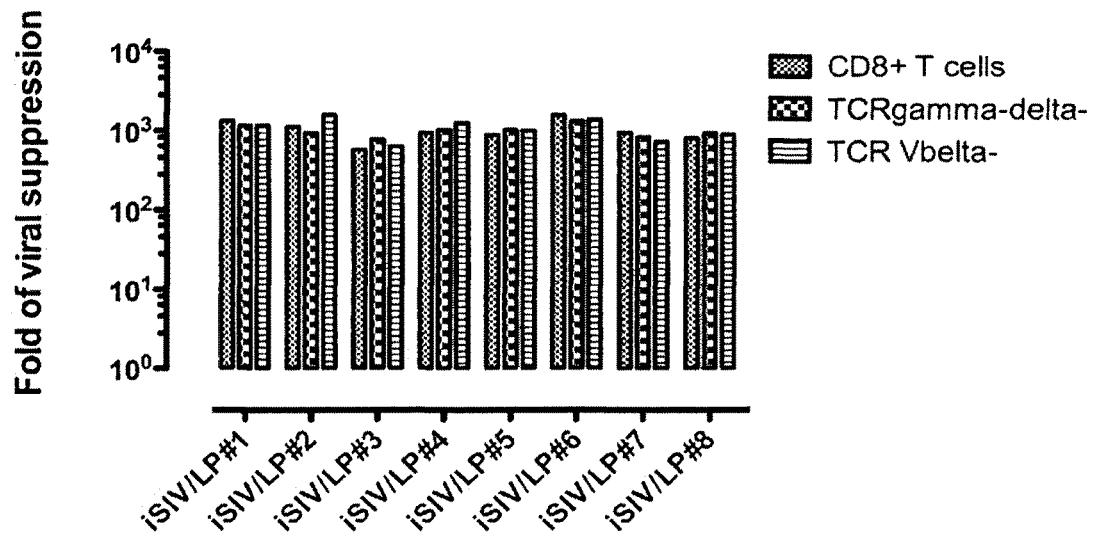

It is established that a CD8+ T cell TCR expression is necessary to recognize MHC-Ib/E-peptide complexes carried by target CD4+ T cells (Sarantopoulos et al., 2004; Van Kaer, 2010). Using an in vitro depletion by antibody-conjugated magnetic microbeads, TCRγδ and Vβ8 were shown not to be involved in CD8+ T cell suppression of viral replication (FIG. 11g). TCRαβ thus appears to play a central role in the recognition of MHC-Ib/E-peptide presentation on infected CD4+ T cells. Moreover, by depleting CD8+ T cells with available anti-human antibodies cross-reacting with membrane CD (for "Cluster Differentiation") antigens of non-human primates (CD7, CD11a, CD16, CD25 (IL-2RA), CD27, CD28, CD39, CD62L, CD95, CD101, CD122 (IL-2RB), CD127 (IL-7R), CD129 (IL-9R), CD137, CD150, CD183 (CXCR3), CD184 (CXCR4), CD195 (CCR5), CD196 (CCR6), CD197 (CCR7), CD215 (IL-15Ra), CD218 (IL-18Ra), CD223 (LAG3), CD226, CD247, CD272, CD277, CD279 (PD-1), CD305 (LAIR1), and CD357), no CD antigen associated with MHC-Ib/E-restricted CD8+ T cells activity could be identified (Table 1). Table 1 below shows the antiviral activity (fold suppression, geometric mean±SE) of CD8+ T cells taken from 8 iSIV/LP-immunized animals before and after depletions of CD antigen-defined subsets* in the first immunisation study (immunisation No. 1).

TABLE 1

| CD antigens value | Undepleted CD8+ T cells | Depleted CD8+ T cells | P |
|---|---|---|---|
| CD7 | 1387 ± 301 | 964 ± 326 | 0.313 |
| CD11a | | 941 ± 377 | 0.568 |
| CD16 | 529 ± 152 | 533 ± 99 | 0.772 |
| CD25 | | 691 ± 258 | 0.490 |
| CD27 | 704 ± 242 | 761 ± 122 | 0.867 |
| CD28 | | 1021 ± 177 | 0.407 |
| CD39 | 970 ± 361 | 1256 ± 354 | 0.710 |
| CD62L | | 1013 ± 302 | 0.832 |
| CD95 | 813 ± 238 | 775 ± 239 | 0.954 |
| CD101 | | 980 ± 197 | 0.613 |
| CD122 | 997 ± 411 | 784 ± 265 | 0.412 |
| CD127 | | 715 ± 339 | 0.545 |
| CD129 | 872 ± 325 | 855 ± 252 | 0.813 |
| CD137 | | 868 ± 306 | 0.852 |
| CD150 | 889 ± 223 | 924 ± 231 | 0.959 |
| CD183 | | 633 ± 198 | 0.354 |
| CD184 | 1452 ± 253 | 1265 ± 447 | 0.841 |
| CD195 | | 1083 ± 295 | 0.374 |
| CD196 | 789 ± 245 | 652 ± 280 | 0.882 |
| CD197 | | 878 ± 247 | 0.789 |
| CD215 | 1221 ± 213 | 1214 ± 445 | 0.621 |
| CD218 | | 739 ± 371 | 0.477 |
| CD223 | 623 ± 293 | 1208 ± 248 | 0.197 |
| CD226 | | 1234 ± 192 | 0.237 |
| CD247 | 914 ± 288 | 940 ± 279 | 0.991 |
| CD272 | | 1056 ± 231 | 0.846 |
| CD277 | 1247 ± 216 | 957 ± 282 | 0.523 |
| CD279 | | 1197 ± 151 | 0.616 |
| CD305 | 798 ± 245 | 1157 ± 241 | 0.233 |
| CD357 | | 820 ± 127 | 0.807 |

*In each batch of experiment, antiviral activity (fold suppression, geometric mean ± SE) of CD8+ T cells taken from 8 iSIV/LP-immunized animals depleted (or not) with 2 anti-CD antigen antibodies was performed.

Figure 12A:
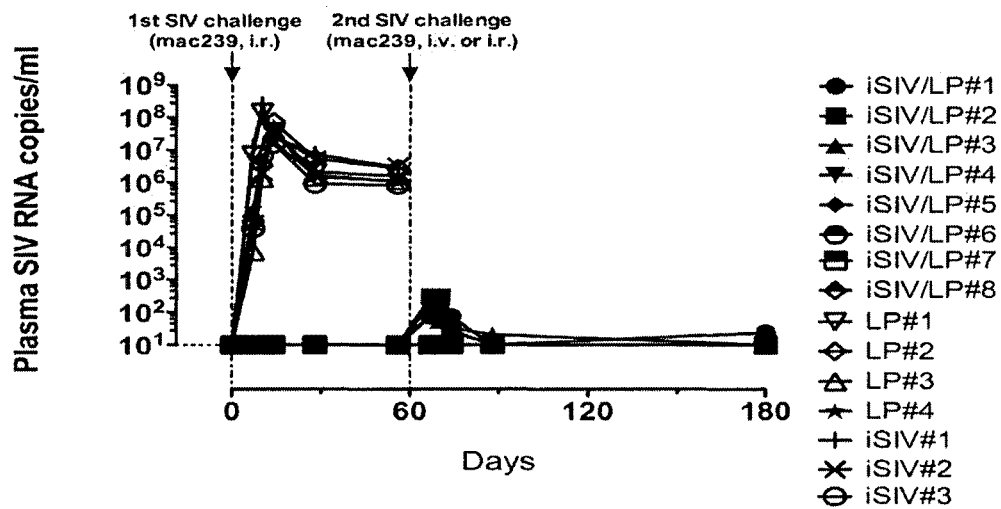
FIG. 12a: Plasma viral load levels (SIV RNA copies per ml of plasma) following intrarectal and intravenous SIV-mac239 challenges in the rhesus macaques pretreated with an oral iSIV/LP as compared to animals pretreated with an oral LP or iSIV.
Figure 12B:
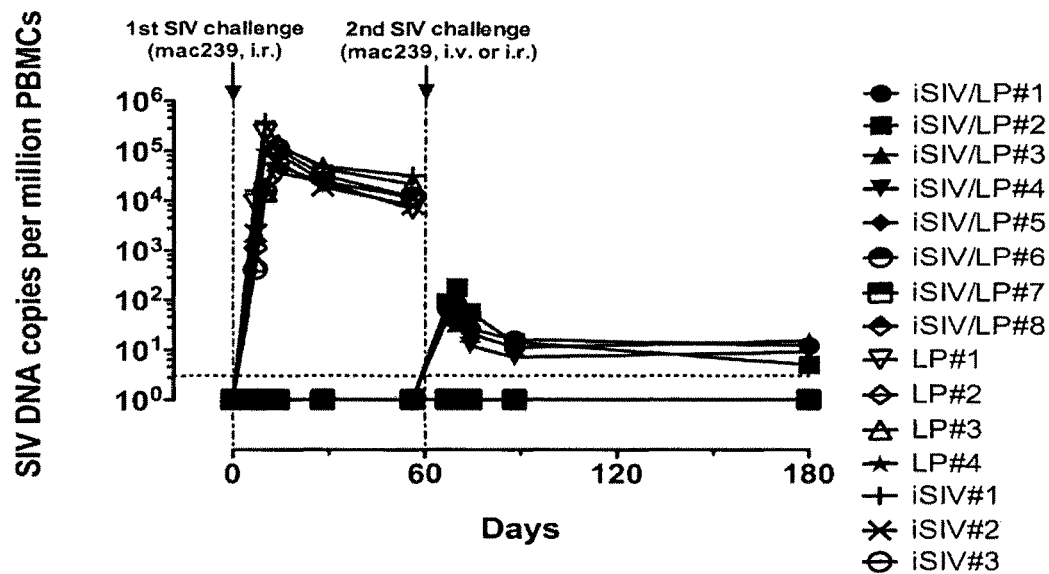
FIG. 12b: Cellular viral load levels (SIV DNA copies per million PBMCs) following intrarectal and intravenous SIV-mac239 challenges in the rhesus macaques pretreated with an oral iSIV/LP as compared to animals pretreated with an oral LP or iSIV.

C-II-III Protection of Animals from Intra-Rectal Challenges by Oral Immunotolerance Three months after the administration of iSIV/LP or control preparations, the 8 iSIV/LP-immunized and the 7 control animals were intrarectally challenged with a single high dose (100,000 TCID$_{50}$) of SIVmac239. Eight out of 8 iSIV/LP-treated animals were protected from intra-rectal challenge of pathogenic SIVmac239 while the 4 iSIV-treated and the 4 LP-treated animals were infected by the same intra-rectal viral challenge (FIGS. 12a and b, left part of the Figures).

C-II-IV Protection of Animals from Intravenous Challenge by Oral Immunotolerance Two months after this first challenge, 4 out of the 8 monkeys received a second challenge via the intravenous route (200 TCID$_{50}$). All of them showed a slight peak of replication (≤200 SIV DNA copies/million PBMC and 200 SIV RNA copies/ml of plasma) at day 10 post-challenge; however by day 30, PBMC SIV DNA had decreased to ≤10 copies/million cells and plasma SIV RNA was undetectable (≤10 copies/ml), indicating the lack of in vivo active replication of the virus (FIGS. 12a and b, right part of the Figures). In contrast, 2 naïve animals which received the same intravenous SIVmac239 challenge (200 TCID$_{50}$) were successfully infected. The 4 remaining monkeys were intrarectally re-challenged (100.000 TCID$_{50}$) and all of them remained fully protected (FIGS. 12a and b, right part of the Figures).

C-II-V Confirmation In Vivo of the Role of CD8+ T Cells

Figure 13A:
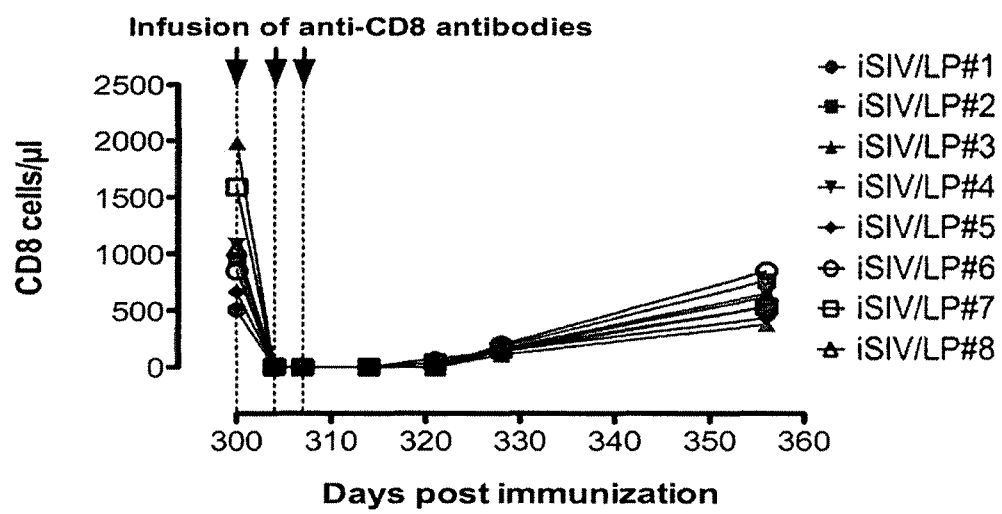
FIG. 13: Depletion of peripheral blood and lymph node CD8+ T cells of the 8 iSIV/LP-treated macaques by infusion of the anti-CD8 antibody cMT807. a, Peripheral blood CD8+ T-cell counts before and after receiving three injections of cMT807; b, % of lymph node CD8+ T cells before and after receiving three injections of cMT807; c, Plasma viral load before and after receiving three injections of cMT807; d, PBMC DNA SIV load before after receiving three injections of cMT807; e, Lymph node SIV DNA load before and after receiving three injections of cMT807.
Figure 13B:
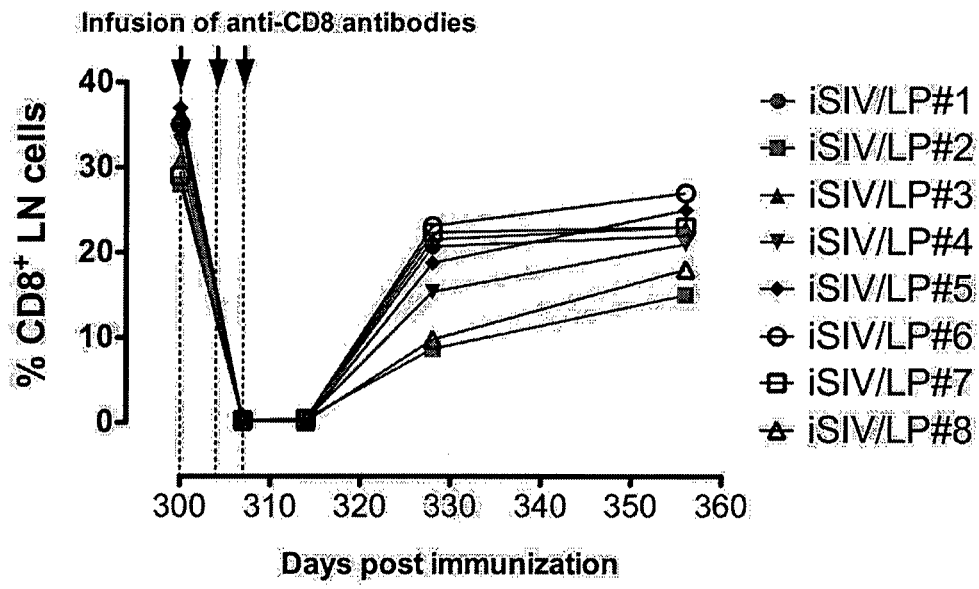
Figure 13C:
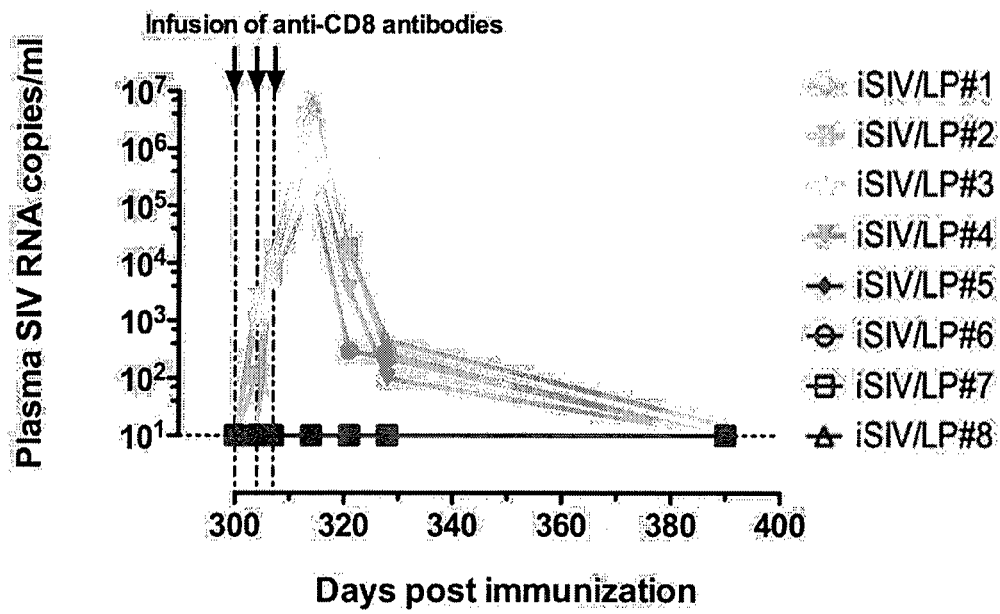
Figure 13D:
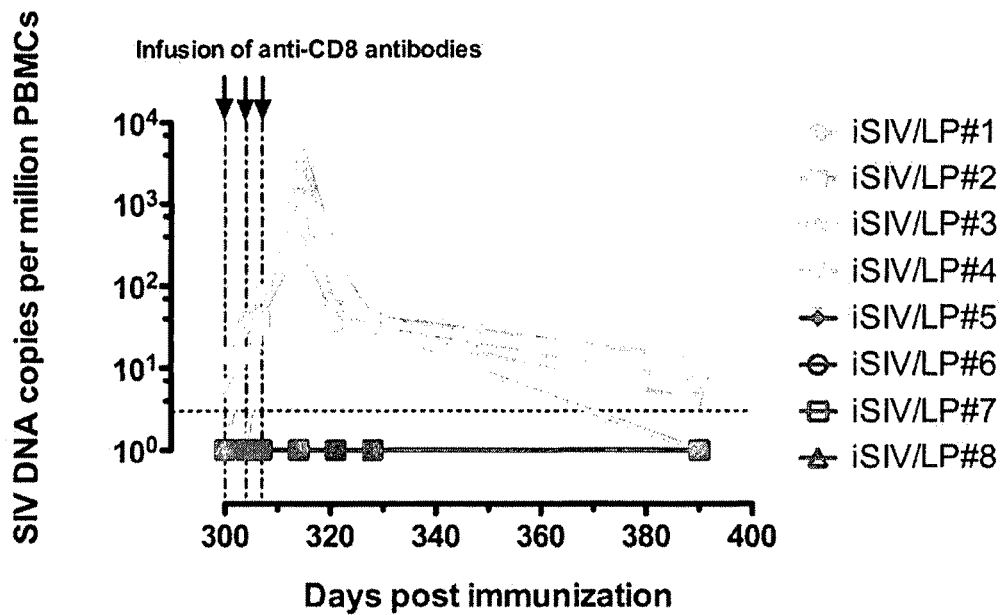
Figure 13E:
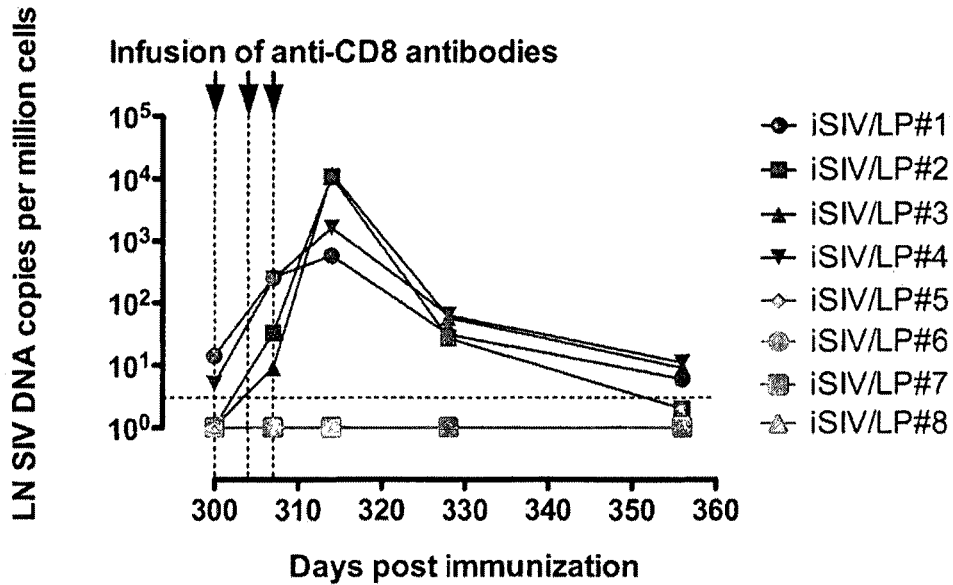

Five months after this second challenge, in order to confirm in vivo the role of CD8+ T cells, 3 intravenous injections of a mouse-human chimeric monoclonal anti-CD8 antibody (cMT-807, Centocor) were given over a period of one week (days 300, 304 and 307 post-immunization) to the 8 already-challenged monkeys to temporarily deplete their CD8+ T cells from peripheral blood and lymphoid organs (FIGS. 13a & b). No viral RNA or DNA emergence was detected in the 4 macaques re-challenged by intrarectal route, demonstrating again their full sterile protection; in contrast, a strong viral replication accompanied the depletion of CD8+ T cells from lymphoid organs of the 4 intravenously challenged animals as shown by their plasma viral loads that peaked at $10^6$ RNA copies/ml and their PBMC and lymph node proviral loads that reached $10^4$ DNA copies/$10^6$ cells by day 15 (the nadir of CD8+ T cells depletion); by days 60-90, when the 4 monkeys had recovered baseline CD8+ T cells concentrations, plasma SIV RNA and PBMC and lymph nodes SIV DNA recovered also baseline levels (FIGS. 13c, d & e). This confirmed the unique role of iSIV/LP-induced CD8+ T cells in the control of in vivo viral replication in intravenously SIV-challenged animals in which replication-competent virus remained latent in presumably in quiescent memory CD4+ T cells.

Figure 14A:
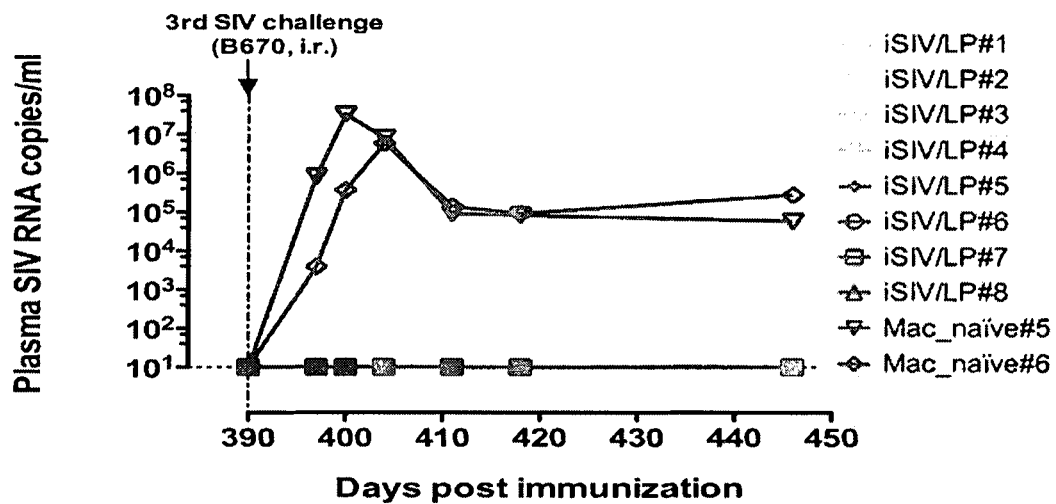
FIG. 14: Plasma (a) and PBMC (b) viral loads following a third intrarectal challenge performed intrarectally with SIVB670 in 8 rhesus macaques immunized with an oral preparation made of iSIV and LP and 2 additional naïve monkeys.
Figure 14B:
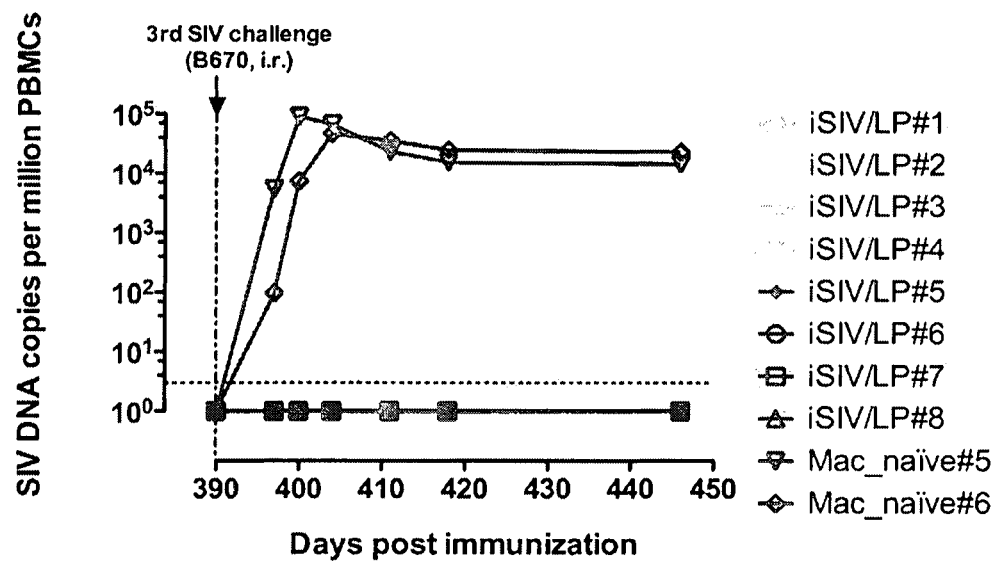

Eight months after the second challenge, the 4 intrarectally rechallenged monkeys as well as the 4 intravenously rechallenged ones received a third challenge, this time via the intrarectal route with SIVB670 (100,000 TCID$_{50}$), a distinct infectious SIV strain. The 8 animals remained fully protected over the next 12 months as shown by their undetectable SIVB670 DNA and RNA levels whereas 2 naïve animals were successfully infected by the same SIVB670 challenge, demonstrating that LP/iSIVmac239-generated MHC-Ib/E-restricted CD8+ T cells were cross-protective through preventing the activation of CD4+ T cells infected by other SIV strains (FIGS. 14a & b).

To determine the duration of efficacy for preventing SIV diseases in the iSIV/LP-treated animals, a second immunization with iSIV/LP was conducted in 8 new macaques of Chinese origin and the in vitro antiviral activity of their CD8+ T cells was checked overtime without SIV challenge. Such an in vitro antiviral activity was detected as from 60 days post-immunization as compared to the control animals either treated with LP (n=4) or iSIV (n=4) alone.

Figure 15A:
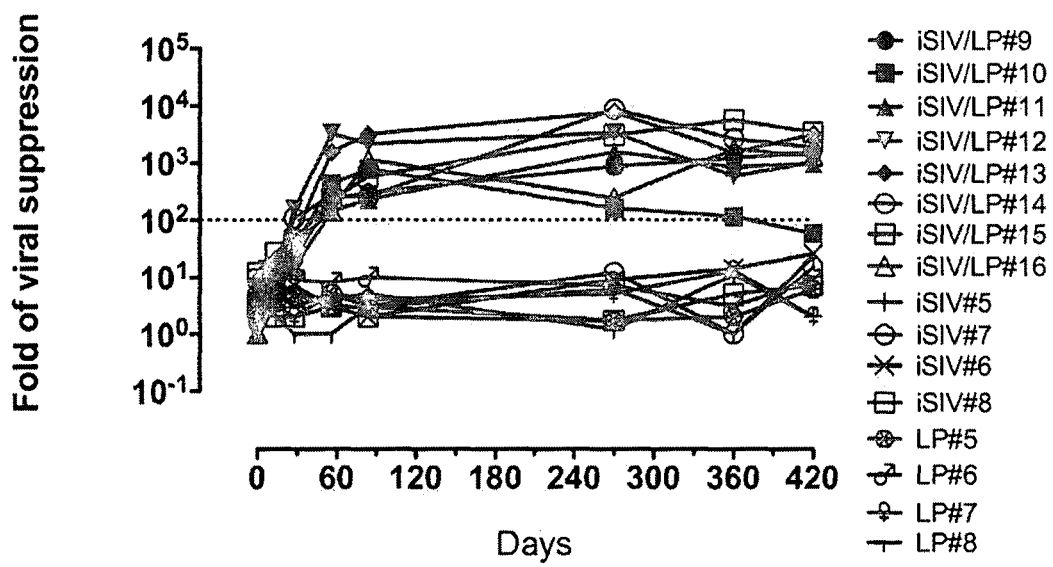
FIG. 15: In vitro and in vivo CD8+ T cell-mediated antiviral activity following intragastric immunization with iSIV and LP (iSIV/LP immunization No. 2). a, Anti-SIV activity (fold of viral suppression) of CD8+ T cells during 60-420 days post-immunization in 8 rhesus macaques that will be challenged intrarectally; b and c, Plasma and cellular viral loads following intrarectal SIVmac239 challenge of those 8 rhesus macaques immunized with an oral iSIV/LP and of 8 control monkeys treated with LP alone (n=4) or iSIV (n=4) alone.
Figure 15B:
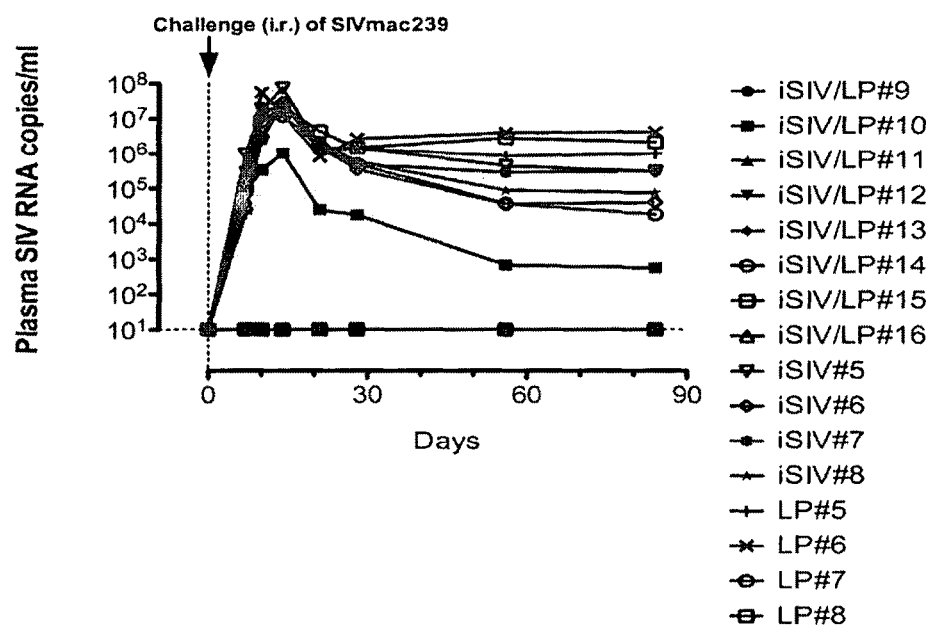
Figure 15C:
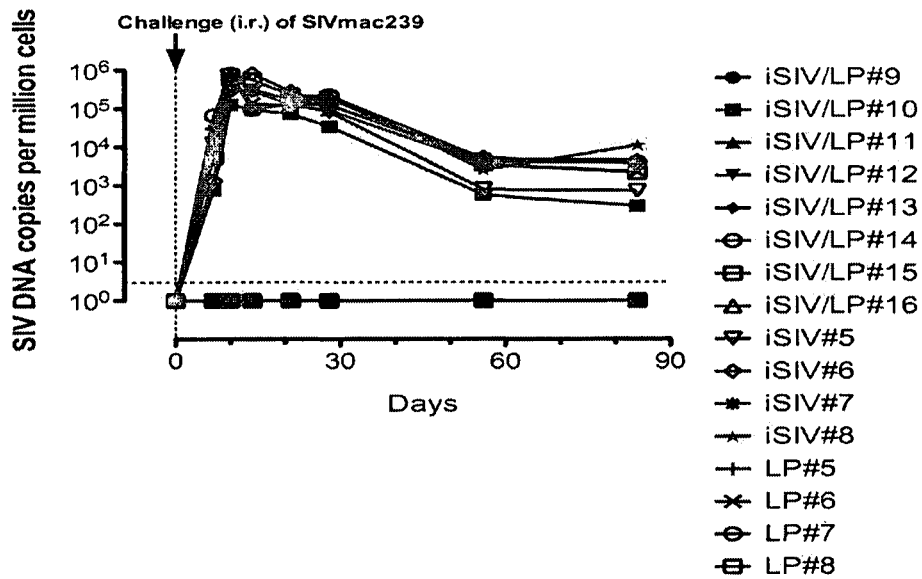
Figure 16A:
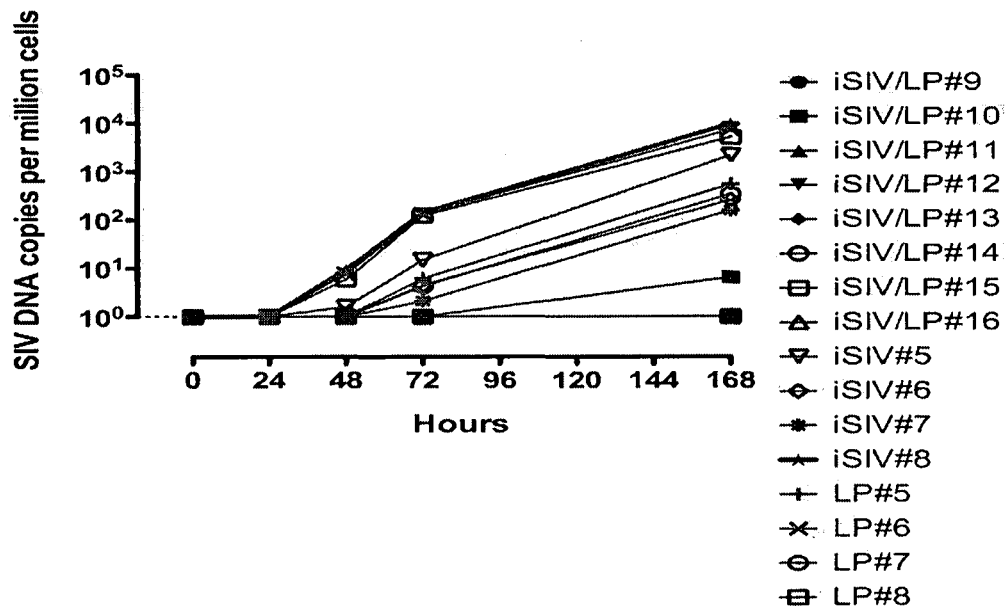
FIG. 16: SIV DNA and RNA loads in rectal mucosa intraepithelial lymphocytes (IPLs) (a-b), lamina propria cells (LPC) (c-d), and in pelvic lymph nodes (PLN) (e) post intrarectal challenge of SIVmac239 in 8 macaques (iSIV/LP immunization No. 2).
Figure 16B:
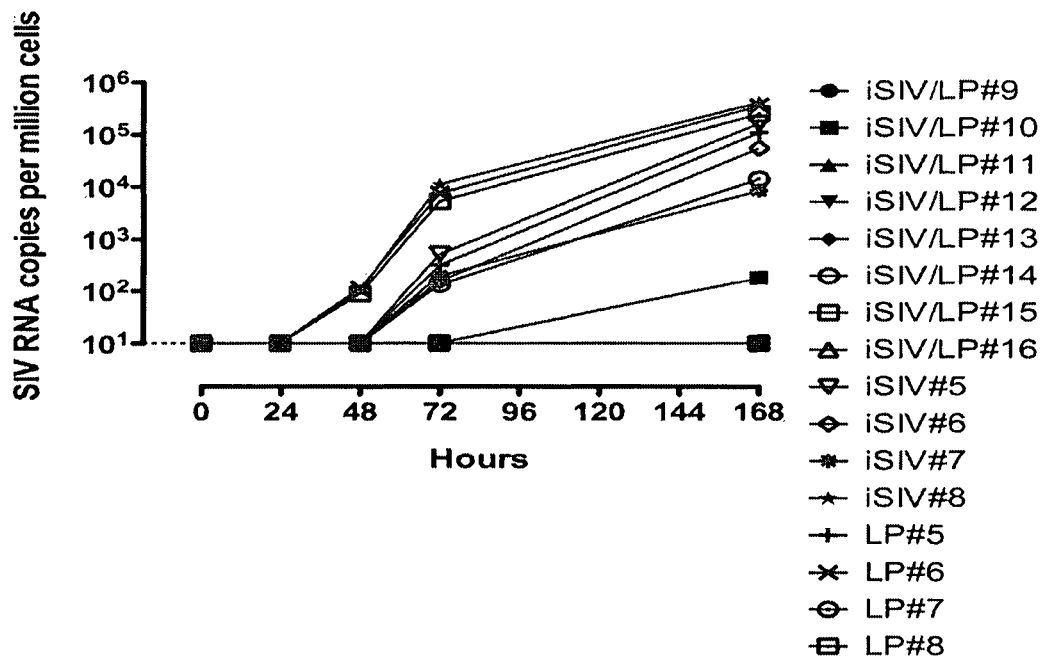
Figure 16C:
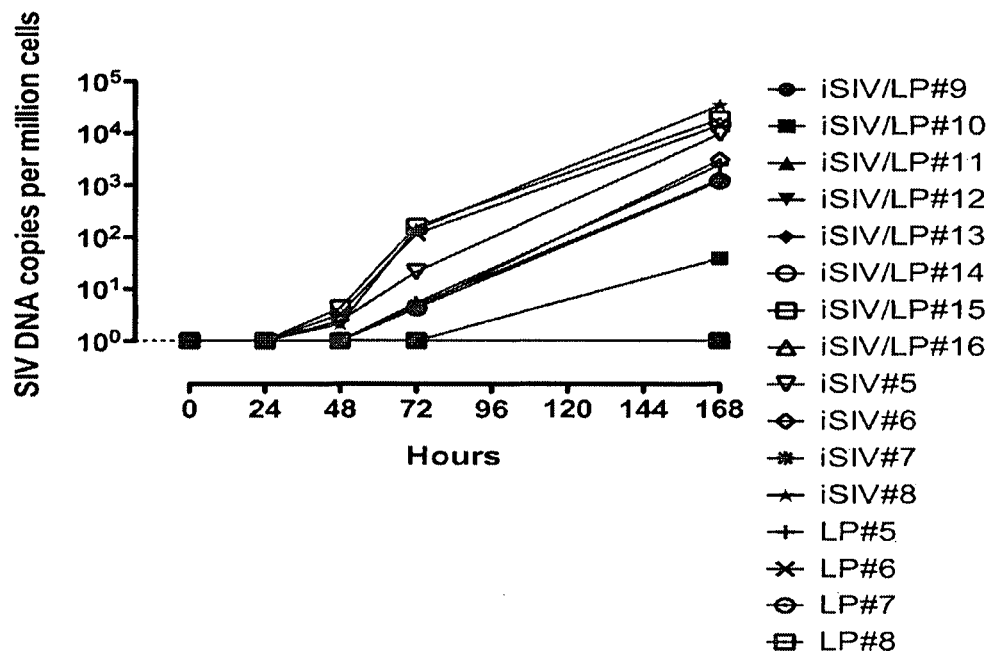
Figure 16D:
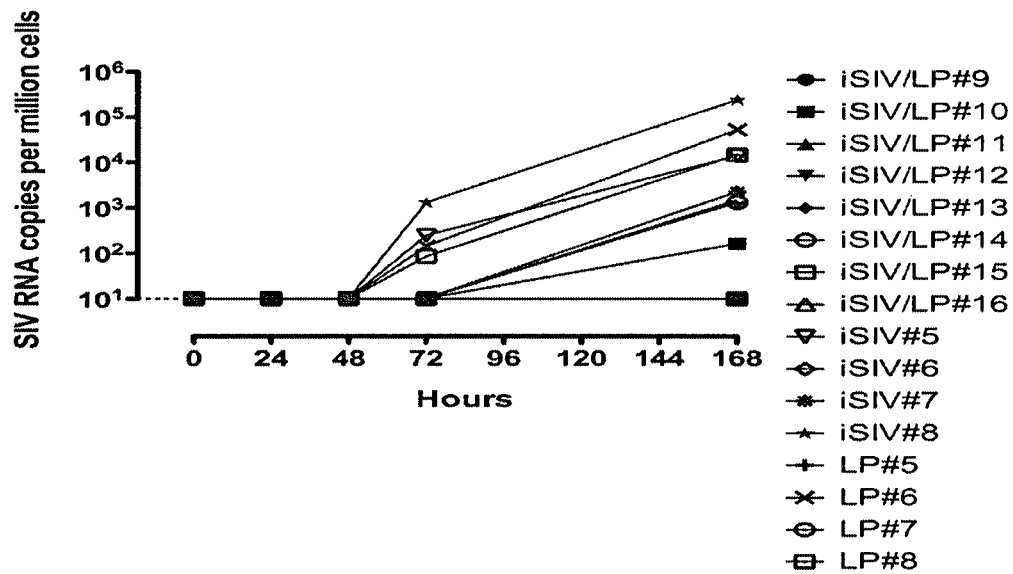
Figure 16E:
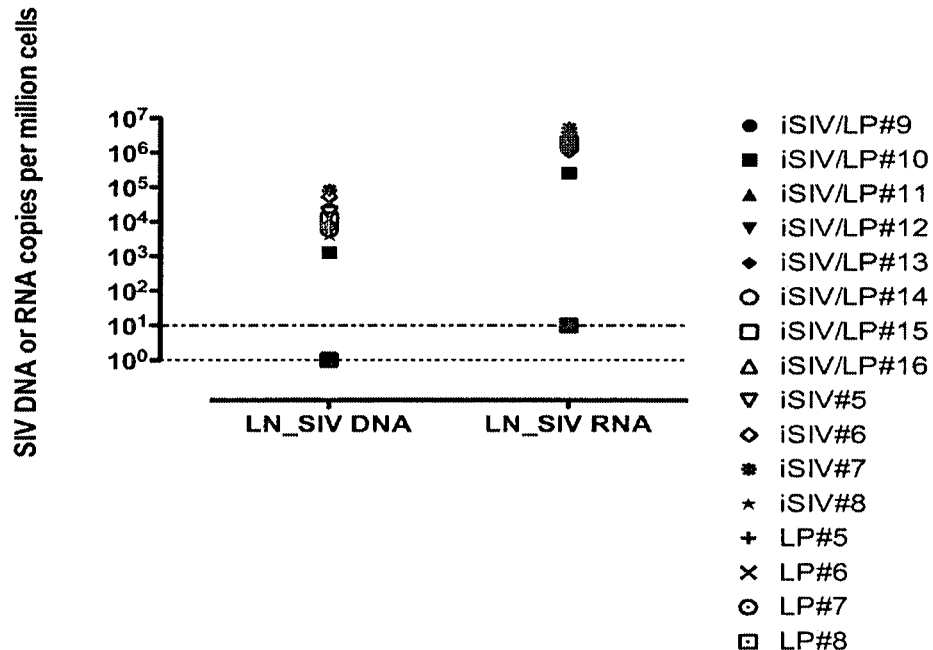

Ex-vivo anti-SIV activity levels were maintained until day 420 in 7 out of 8 monkeys while the antiviral activity of one monkey progressively decreased from day 360 to reach baseline levels of control monkeys by day 420 (FIG. 15a). On day 420 post-immunization, the 16 animals were intrarectally challenged with 100,000 TCID$_{50}$ of SIVmac239. Seven out of the 8 iSIV/LP-immunized animals acquired a sterile immunity without any SIV RNA and DNA emergence in plasma and PBMC (FIGS. 15b & c), as well as in rectal mucosa lymphocytes (where they were measured from day 1 post challenge) and pelvic lymph nodes (FIG. 16a to 16e) while one immunized monkey was fully infected. Importantly, the evolution of the ex-vivo antiviral activity of the 8 vaccinated monkeys allowed to predict from day 360 post immunization (i.e., 60 days before their challenge) the 7 protected monkeys and the unprotected one (FIGS. 15a to c).

C-II-VI Conclusions

It is disclosed herein, in the macaque model, that the administration of inactivated SIVmac239 (iSIV) and commensal *Lactobacillus plantarum* (LP) (referred to as a tolerogenic adjuvant) generates MHC-Ib/E-restricted CD8+ T cells that induced the suppression of activation of SIV antigen-presenting CD4+ T cells and thereby the suppression of SIV replication and the protection of macaques from SIV challenges.

A mixture made of inactivated iSIV and LP was administered intragastrically to a total of 16 animals and 15 controls. Four to 14 months later, all animals were challenged intrarectally with pathogenic SIVmac239.

Full protection against SIV infection was observed in 15 out of 16 iSIV/LP-administered animals; in contrast, infection was established in all control animals and one vaccinated monkey. The unprotected monkey can be predicted by an ex vivo antiviral assay 60 days before the intrarectal challenge. Eight protected animals remained protected after a second SIVmac239 challenge given intravenously in 4 monkeys and intrarectally in the other 4.

The 8 iSIV/LP-delivered animals had complete lack of SIV-specific peripheral blood CD4+ T cell proliferation and did not raise any systemic SIV-specific antibodies (IgG, IgM, or IgA).

Moreover, their SIV-specific peripheral blood CD8+ T cell had several particularities:
1) they proliferated well but without interferon-γ secretion upon to in vitro stimulation;
2) they strongly suppressed the activation of acutely infected autologous CD4+ T cell;
3) both functions remained unchanged after depletion of CD25+ cells;
4) they inhibited also SIV replication in acutely infected allogenic CD4+ T cells; and
5) their suppressive/inhibiting action was MHC-Ib/E-restricted.

These results show that intra-gastric co-administration of iSIV and LP allows macaques to develop virus-specific non-cytotoxic MHC-Ib/E-restricted CD8+ regulatory T cells which generate an SIV-specific immunotolerance and that very surprisingly such a virus-specific immunotolerance is associated with vaccine protection of animals against the establishment of SIV infection.

It is shown hereinabove that the pharmaceutical composition according to the present invention prevents HIV and SIV infections in humans/mammals. This preventive action is obtained in macaques by inducing a "Ts" immunotolerance in the tolerogenically-vaccinated subjects (i.e., the mammals having been administered the pharmaceutical composition). Said "Ts" immunotolerance is herein demonstrated to involve virus-specific non-cytotoxic MHC-Ib/E-restricted suppressive CD8 regulatory T cells, the presence and the activity of which being shown to:
 inhibit SIV replication in acutely-infected CD4+ T cells of macaques having been administered the pharmaceutical composition of the present invention (in vitro); and/or
 prevent SIV replication in tolerogenically-vaccinated macaques that are challenged with infectious SIV (in vivo).

REFERENCES

Morgan C, et al. Plos Medicine 2008, 5:1200-1204
Marcondes M C, et al. Viral Immunol 2006,19:679-689
Stahl-Hennig C, et al. J Med Primatol 2007,36:195-205
Chen S, et al. Zhongguo Yi Xue Ke Xue Yuan Xue Bao 2008,30:156-160
Hu et al., JAMA 275:210-216, 1996
Korber et al., Science 280:1868-1871, 1998
Papathanasopoulos M A, et al. Virus Genes 2003,26:151-163
RAVIV et al. *J. Virol.*, vol. 79(19), p: 12394-12400, 2005
Chien, Novel Drug Delivery Systems, Ch. 4 (Marcel Dekker, 1992)
*Ullmann's Encyclopedia of Industrial Chemistry*, 6$^{th}$ Ed. (various editors, 1989-1998, Marcel Dekker)
*Pharmaceutical Dosage Forms and Drug Delivery Systems* (ANSEL et al., 1994, WILLIAMS & WILKINS)
Ebadi, Pharmacology, Little, Brown and Co., Boston, Mass. (1985)
WONG et al. *Proc. Natl. Acad. Sci. U.S.A.*, vol. 104(8), p: 2591-2595, 2007
Fuller. J. Appl. Bacteriol. 66:365-378 (1989)
I. Mederle, R. Le Grand, B. Vaslin et al., Vaccine 21 (27-30), 4153 (2003)
W. Lu, X. Wu, Y. Lu et al., Nature medicine 9 (1), 27 (2003)
A. S. Fauci, Nature 384 (6609), 529 (1996)
Faria and Weiner, Immunol Rev 206, 232 (2005)
Mestecky et al., J Immunol 179 (9), 5633 (2007)
HOFT et al. (*J Infect Dis., vol.* 198(10), p: 1491-1501, 2008)
WANG et al (*Med Microbiol Immunol.,* 2008 May 20)
Rerks-Ngarm et al. N. Engl. J. Med. *Vaccination with ALVAC and AIDSVAX to prevent HIV-1 infection in Thailand,* 2009 Oct. 20 (epub)
McElrath et al. The Lancet, Volume 372, Issue 9653, Pages 1894-1905, 29 Nov. 2008
Tsai et al., Laboratory animal science 43 (5), 411 (1993)
Wei Li Lee et al. Small, (p 1003-1011) Published Online: Mar. 31, 2010 12:16 PM DOI: 10.1002/smll.200901985
Delie F. Adv Drug Deliv Rev. 1998; 34:221-233
Mathiowitz et al. Nature. 1997; 386:410-414
Goldberg et al. Nat Rev Drug Discov. 2003; 2:289-295
Fasano et al. J Clin Invest. 1997; 99:1158-1164
Sandri et al. Eur J Pharm Biopharm. 2007; 65:68-77
Chickering et al. J Control Release. 1997; 48:35-46
Ponchel et al. Adv Drug Deliv Rev. 1998; 34:191-219
Plotkin et al. Vaccines, Saunders Elsevier Fifth edition, 2008, pages 215 & 216
Korin and Zack, Journal of virology 73 (8), 6526 (1999)
Vatakis et al., Journal of virology 83 (12), 6222 (2009a)
Vatakis et al., Journal of virology 83 (7), 3374 (2009b)
Andrieu and Lu, Immunol Today 16 (1), 5 (1995)
Sacha et al., J Immunol 178 (5), 2746 (2007)
Schmitz et al., The American journal of pathology 154 (6), 1923 (1999)
Liew et al., 2010. Journal of Biotechnology 150:224-231
Plummer and Manchester, 2010. Viral nanoparticles and virus-like particles: platforms for contemporary vaccine design. John Wiley & Sons, Inc. WIREs Nanomedicine and Nanobiotechnology. DOI: 10.1002/wnan.119
Ke-Qin Xin et al. Blood 102 (1), 223-228 (1 Jul. 2003)
Jae-Sung Yu et al. Clinical and Vaccine Immunology 13(11), 1204-1211 (November 2006)
Scholzen and Gerdes. J. Cell Physiol. 182, 311-322 (March 2000)
Muhl, et al. MHC class I alleles influence set-point viral load and survival time in simian immunodeficiency virus-infected rhesus monkeys. J Immunol 169, 3438-3446 (2002)
Loffredo et al. Mamu-B*08-positive macaques control simian immunodeficiency virus replication. Journal of virology 81, 8827-8832 (2007)
Sarantopoulos et al. Qa-1 restriction of CD8+ suppressor T cells. The Journal of clinical investigation 114, 1218-1221 (2004)
Jiang et al. HLA-E-restricted regulatory CD8(+) T cells are involved in development and control of human autoimmune type 1 diabetes. The Journal of clinical investigation 120, 3641-3650 (2010)
Van Kaer, L. Comeback kids: CD8(+) suppressor T cells are back in the game. The Journal of clinical investigation 120, 3432-3434 (2010)
Marchetti, P., et al. Mitochondrial permeability transition is a central coordinating event of apoptosis. The Journal of experimental medicine 184, 1155-1160 (1996)

The invention claimed is:

1. An oral pharmaceutical composition comprising a mixture of inactivated HIV virus particles and non-pathogenic *Lactobacillus* bacteria, in amounts effective for inducing antigen-specific immunotolerance.

2. A method for inducing antigen-specific immunotolerance, comprising administering to a human in need thereof a pharmaceutically effective amount of a pharmaceutical composition according to claim 1.

3. A pharmaceutical kit for preventing and/or treating an HIV disease in a human in need thereof, comprising:

in a first container, inactivated HIV virus particles; and in a second container, non-pathogenic *Lactobacillus* bacteria, said antigen and said *Lactobacillus* bacteria each being in a pharmaceutically acceptable carrier for oral administration, and being present in amounts effective for inducing antigen-specific immunotolerance.

4. The pharmaceutical composition according to claim 1, wherein said HIV is HIV-1 or HIV-2.

5. The pharmaceutical composition according to claim 1, wherein said bacteria are *Lactobacillus acidophilus, Lactobacillus bulgaricus, Lactobacillus casei, Lactobacillus paracasei, Lactobacillus johnsonii, Lactobacillus plantarum, Lactobacillus reuteri, Lactobacillus rhamnosus, Lactobacillus brevis, Lactobacillus gasseri*, or *Lactobacillus salivarius.*

6. The pharmaceutical composition according claim 1, wherein:

the amount of inactivated HIV virus particles in the pharmaceutical composition is from about $10^6$ to about $10^{12}$ per ml of said mixture; and/or the amount of said non-pathogenic bacteria bacterium in the pharmaceutical composition is from about $10^4$ to about $10^{14}$ CFU per ml of said mixture.

7. The pharmaceutical composition according to claim 1, wherein the ratio in said mixture of said virus particles to said bacterium is from about 1:10 to about 1:1000.

8. The pharmaceutical composition according to claim 1, wherein the ratio in said mixture of said virus particles to said bacterium is about 1:100.

9. The method according to claim 2, wherein said HIV disease is AIDS or seroconversion.

10. The method according to claim 2, wherein said composition is administered once or several times consecutively.

11. The method according to claim 2, wherein:

a dose of about $10^8$ to $10^{14}$ inactivated HIV virus particles is administered per day to said human; and/or a dose of about $10^6$ to about $10^{16}$ CFU of said non-pathogenic bacteria is administered per day to said human.

* * * * *